(12) United States Patent
Li et al.

(10) Patent No.: US 9,604,987 B2
(45) Date of Patent: Mar. 28, 2017

(54) SYNTHESIS OF AUTOPHAGY INDUCING COMPOUND AND THE USES THEREOF

(71) Applicant: Hong Kong Baptist University, Hong Kong (HK)

(72) Inventors: Min Li, Hong Kong (HK); Liang Feng Liu, Hong Kong (HK); Ju Xian Song, Hong Kong (HK); Hong Jie Zhang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 14/927,483

(22) Filed: Oct. 30, 2015

(65) Prior Publication Data

US 2016/0046629 A1 Feb. 18, 2016

Related U.S. Application Data

(63) Continuation-in-part of application No. 13/420,628, filed on Mar. 15, 2012, now abandoned.

(51) Int. Cl.
| | | |
|---|---|---|
| A61K 31/44 | (2006.01) |
| C07D 471/20 | (2006.01) |
| A61K 31/437 | (2006.01) |
| A61K 45/06 | (2006.01) |

(52) U.S. Cl.
CPC .......... *C07D 471/20* (2013.01); *A61K 31/437* (2013.01); *A61K 45/06* (2013.01); *Y02P 20/582* (2015.11)

(58) Field of Classification Search
CPC .. A61K 45/06; A61K 31/437; A61K 2300/00; C07D 471/20; Y02P 20/582
See application file for complete search history.

(56) References Cited

FOREIGN PATENT DOCUMENTS

WO WO2008122038 A1 * 10/2008

OTHER PUBLICATIONS

Sakakibara et al ( Phytomedicine, 1999, 6(3), 163-168).*

* cited by examiner

*Primary Examiner* — Jason Sims
*Assistant Examiner* — Ibrahim D Bori
(74) *Attorney, Agent, or Firm* — Spruson & Ferguson (Hong Kong) Limited

(57) ABSTRACT

The present invention relates to a composition comprising compound of formula CB6 or CB8, (CB6)

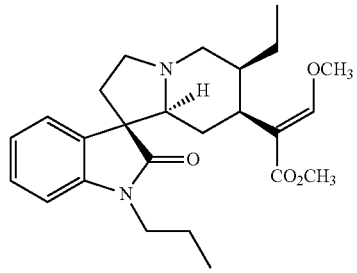

(CB8)

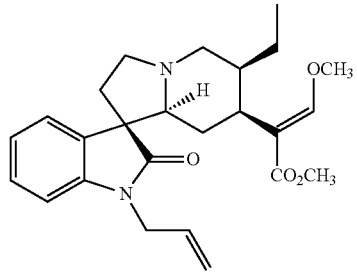

the pharmaceutically-acceptable carrier, solvent, the salts thereof or a combination thereof which is used to treat autophagy-associated diseases such as Alzheimer's disease, Parkinson's disease, Huntington's disease, etc. The present invention also relates to a method of treating these diseases by administering a therapeutically-effective amount of the compound to the subject in need of the treatment. The present invention further relates to the use of this compound in preparation of the composition to treat the diseases.

9 Claims, 28 Drawing Sheets

SYNTHESIS OF AUTOPHAGY INDUCING COMPOUND AND THE USES THEREOF

CROSS-REFERENCE TO RELATED APPLICATIONS

The present application is a continuation-in-part application of U.S. non-provisional application Ser. No. 13/420,628 filed on Mar. 15, 2012, which claims priority of U.S. provisional application No. 61/466,479 filed on Mar. 23, 2011; and the disclosures of which are hereby incorporated by reference by their entirety.

TECHNICAL FIELD

The present invention relates to a composition including a synthesized autophagy inducing compound. In particular, the present invention relates to a composition including the autophagy inducing compound used to degrade abnormal protein deposit in the nervous system by inducing autophagy and related methods of treatment, such as treating neurodegenerative diseases associated with abnormal protein aggregation and/or deposition and cancer.

BACKGROUND

Macroautophagy, herein referred to as autophagy, is a highly conserved process for cellular degradation and recycling of cytosolic contents to maintain cellular homeostasis. Autophagy substrates are generally cellular organelles, long-lived proteins and aggregate-prone proteins. Due to its functionality to clear cytosolic contents, this highly conserved process has been shown to be a promising approach for treatment of diseases characterized by the formation of intracellular aggregates, such as aging of the brain and neurodegeneration. Dysfunction of the autophagy pathway has also been implicated in various cancers.

Aggregate-prone disorders are characterized by the formation of intracellular aggregates in specific tissues. For example: neurodegenerative diseases are associated with the accumulation of abnormal protein aggregates in affected regions of the brain. One example of a disease-causing, aggregate-prone protein is alpha-synuclein ($\alpha$-syn). Overexpression of $\alpha$-syn due to duplication or triplication of the $\alpha$-syn gene locus has been shown to result in familial form of Parkinson's disease (PD). Point mutations (A53T and A30P) of $\alpha$-syn increase the aggregation propensity thereof also lead to early onset of familial PD. Moreover, overexpressions of wild type (WT) and mutant $\alpha$-syn in transgenic mice as well as transgenic flies have been found to cause progressive locomotor defects with dopaminergic neuron loss and intracytoplasmic inclusions. It is also believed that accumulation of $\alpha$-syn oligomers, which are intermediates of fibrillar aggregates or inclusion formation are toxic and lead to direct neuronal death. These findings illustrate that $\alpha$-syn as valuable therapeutic target for the treatment of PD and other synucleinopathies.

Other examples of aggregate-prone disorders include Alzheimer's disease; Hungtinton's disease; spinocerebellar ataxia types 1, 2, 3, 6, 7 and 17; spinobullar muscular atrophy; dentatorubral-palli-doluysian atrophy; different forms of dementia that are caused by mutations in the neuronal protein tau; forms of motor neuron disease caused by mutations in superoxide dismutase 1 (SOD1) and forms of peripheral neuropathy caused by mutations in peripheral myelin protein 22 (PMP22).

Apart from $\alpha$-syn, it is well-established that other large disease-causing protein aggregates like oliogomeric $\alpha$-syn, tau and mutant huntingtin, are also relied greatly on autophagy pathway for clearance since they cannot go through the narrow core of proteasomes for degradation. Furthermore, recent reports using mutant mice lacking the autophagy-related genes atg5 or atg7 indicate basal autophagy has an important role in neuronal functions.

Certain bacterial and viral infections may also be treatable by autophagy upregulation, since the pathogens can be engulfed by autophagosomes and transferred to lysosomes for degradation. For instance: *Mycobacterium tuberculosis*; Group A *Streptococcus* and Herpes Simplex Virus Type I.

Approaches to activate autophagy for therapeutic applications, such as treating neurodegenerative diseases and cancers have been explored in the art. For instance: Bradner et al. (WO2008/122038) discloses various modulators of autophagy such as compounds with a bis-indolyl maleimide core for the treatment or prevention of neurodegenerative diseases, proliferative diseases as well as infectious diseases; Rubinsztein et al. (US20070155771) describes the use of rapamycin for the treatment of conditions characterized by formation of intracellular protein aggregates by stimulation of autophagic activity and Yuan et al. (US2010/0267704) discloses treatments using autophagy inducing compounds including Loperamide, Amiodarone, Niguldipine, Pimozide.

However, current small molecules which upregulate autophagy in mammalian brains such as rapamycin, are specific mTOR inhibitors. TOR proteins are known to control several cellular processes besides autophagy in organisms from yeast to human. Thus, long-term use of these mTOR dependent small molecule autophagy inducers is likely to contribute to complications. Moreover, autophagy in the central nervous system is also known to be regulated differently from that in non-neuronal cells and the induction thereof in neuronal cells has been shown to be more difficult than in non-neuronal cells. These classical autophagy inducers either fail to induce autophagy in the cortex of mouse brains or induce only mild autophagy in neurons.

Corynoxine B (Cory B), one of the Uncaria oxindole alkaloids has been used as a component of various compositions to induce various biological outcomes, such as protective effects on ischemia-induced neuronal damage; inhibition of Listeriolysin O-induced nitric oxide and endothelin-1 release and prevention angiotensin II induced proliferation. Nevertheless, there is no teaching or suggestion in the prior art relating to this kind of compounds (oxindole alkaloids) to induce autophagy.

Accordingly, there is a need for a potent agent which specifically induces autophagy independent of mTOR in neurons for the treatment of diseases that can benefit from autophagy, including but not limited to neurodegenerative disorders, immunological diseases, cardiac diseases and cancer.

SUMMARY OF THE INVENTION

The present invention relates to novel application of a compound of formula (I),

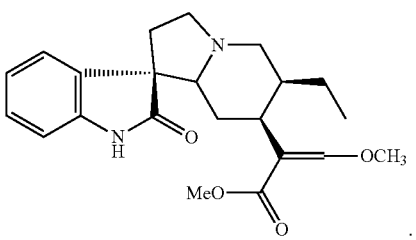

(I)

Applicants of the subject application are the first to demonstrate that the compound of formula (I) is a potent autophagy inducer and capable of degrading abnormal cytosolic contents, especially aggregate-prone proteins in neurons, thereby treating diseases that can benefit from autophagy, such as neurodegenerative diseases and cancer.

The first aspect of the present invention relates to a pharmaceutical composition comprising the compounds of formula (I) (also called CoryB and a pharmaceutically acceptable salt thereof, that is used for treatment of diseases that can benefit from degradation of cytoplasmic proteins, organelles or pathogens by inducement of autophagy. In particular, the compound of formula (I) induces autophagy in neurons. The compound of formula (I) of the present invention is a kind of tetracyclic oxindole alkaloid isolated from Uncaria species including, but not limited to Uncaria rhynchophylla, Uncaria macrophylla Wall, Uncaria sinensis (Oliv.) Havil and Uncaria tomentosa. The functional groups of this compound may be substituted by a moiety including but not limited to hydrogen, —$CH_3$, and glucose known to a skilled artisan, wherein the autophagy induction activity is maintained. The compound itself may be modified such that commonly used carriers, salts or esters known to one skilled in the art (e.g. methyl acetate, ethyl acetate) can be incorporated therein to allow different modes of administration. This compound is also small enough to pass through the blood-brain barrier in order to target specific cells/tissue in the nervous system, where abnormal protein aggregation and/or deposition occur. Evidences of the ability of such kind of compounds to pass through the blood-brain barrier is also presented in "The distribution of isorhynchophylline in the tissues of the rats and the determination of its plasma half-life time", ACTA ACADEMIAE MEDICINAE ZUN YI. 2001, 24:119-120.

The present invention also relates to other tetracyclic oxindole alkaloids isolated from Uncaria species including, but not limited to corynoxine (formula II) as autophagy inducers for treating a disease that can benefit from autophagy:

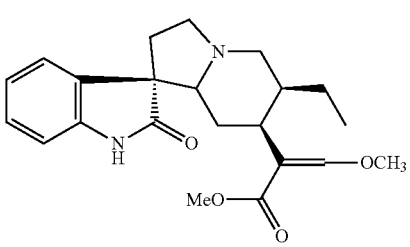

(II)

In another aspect, the present invention features a pharmaceutical compositions comprising an autophagy inducing compound in an amount effective for treating a disease that can benefit from autophagy, wherein the compound is at least one compound selected from the group including:

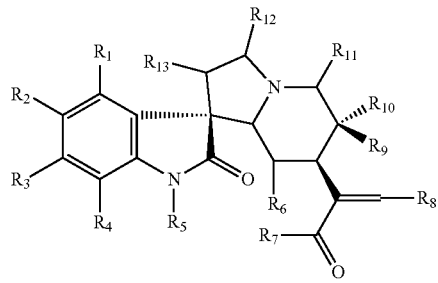

(III)

and

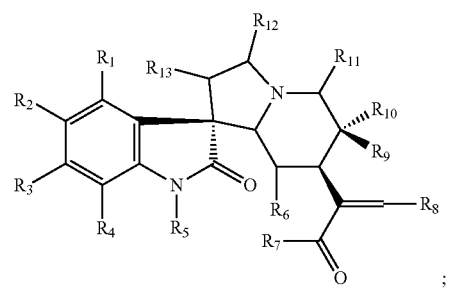

(IV)

A compound of formula IV or formula V, wherein $R_1$, $R_2$, $R_3$, $R_4$, $R_5$, $R_6$, $R_{11}$, $R_{12}$ and $R_{13}$ are each independently selected from hydrogen, hydroxyl, halogen, C1-6 alkyl and C1-6 haloalkyl; $R_7$ and $R_8$ are each independently selected from methoxyl and hydroxyl; $R_9$ and $R_{10}$ are each independently selected from hydrogen, hydroxyl, halogen, C1-6 alkyl.

The present invention includes one or more other therapeutic agent(s) known to treat a disease that can benefit from inducement of autophagy, such as chemotherapeutic agents known in the art; or a compound that may potentiate the autophagy inducing activity of a compound of formula (I-V). The present invention further comprises one or more of a pharmaceutically-acceptable carrier, solvent, excipient, adjuvant and/or prodrug.

The second aspect of the present invention relates to methods for treatment of diseases that can benefit from inducement of autophagy by administration of a therapeutically effective amount of the pharmaceutical composition of the present invention to a subject in need thereof. In one embodiment of this aspect, the disease is caused by abnormal protein aggregation and/or deposition in the nervous system, especially among the neuronal cells. In another embodiment, the disease is cancer, wherein the induction of autophagy would inhibit cell growth or remove organelles damages by reactive oxygen species, such as mitochondria or tumor cells and the autophagy target is cancerous cells or tumor cells. In another embodiment of this aspect, the method further comprises administering one or more other therapeutic agent known to treat diseases that benefit from inducement of autophagy.

The third aspect of the present invention relates to a method of using the compounds of formula (I-IV) in the preparation of a pharmaceutical composition for treating diseases that can benefit from autophagy enhancement.

BRIEF DESCRIPTION OF THE DRAWINGS

FIG. 17.

ABBREVIATIONS

Figure 1A:
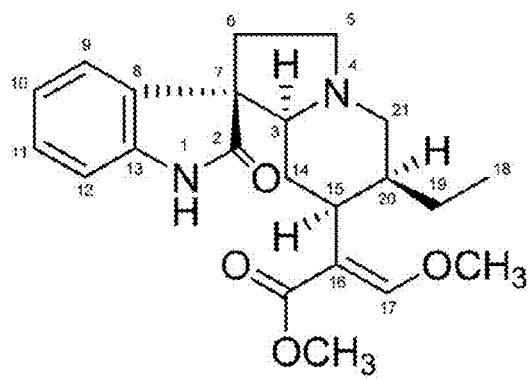
FIG. 1: Chemical structure of Corynoxine B (Cory B) (FIG. 1A); Western blot analysis of the expression level of autophagy marker, LC3-II, in different neuronal cell lines including N2a (FIG. 1B), PC12 (FIG. 1C) and SH-SY5Y (FIG. 1D) induced by 0-25 μM Cory B for 24 hours; Fluorescent images of GFP signal (FIG. 1E) and number of GFP-LC3 puncta per cell (FIG. 1F).

α-syn: alpha-synuclein;
BiFC: Bimolecular Fluorescence Complementation
CQ: chloroquine;
DA: dopaminergic;
GFP: enhanced green fluorescent protein;
HA: hyaluronan Cory B: Corynoxine B;
3-MA: 3-Methyladenine;
(MAP)LC3: microtubule-associated protein 1 light chain 3;
mTOR: mammalian target of rapamycin;
PD: Parkinson's disease;
Tf-LC3: tandem fluorescent LC3
RFU: Relative Fluorescence Unit
RFP: Red Fluorescence Protein

DEFINITIONS

"a," "an," and "the" as used herein include "at least one" and "one or more" unless stated otherwise. Thus, for example, reference to "a pharmacologically acceptable carrier" includes mixtures of two or more carriers as well as a single carrier, and the like.

The terms "aggregate-prone proteins" and "autophagy substrate" are used interchangeably, referring to cytosolic proteins that are prone to aggregation and deposition and their aggregation are disease causing. Examples include, but are not limited to α-synuclein, Huntingtin, tau, SOD1 and PMP22 and the mutant and variant forms thereof.

The term "autophagy" refers to macroautophagy, unless stated otherwise, which is the catabolic process involving the degradation of a cell's own components; such as, long lived proteins, protein aggregates, cellular organelles, cell membranes, organelle membranes, and other cellular components. The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. The term autophagy may also refer to one of the mechanisms by which a starving cell re-allocates nutrients from unnecessary processes to more essential processes. Also, for example, autophagy may inhibit the progression of some diseases and play a protective role against infection by intracellular pathogens.

The diseases that benefit from autophagy inducement are those that can be treated by the inventions as disclosed herein. The diseases include aggregate-prone disorder which represents any disease, disorder or condition associated with or caused by abnormal protein aggregates that are not sufficiently destroyed by a natural autophagy process in an organism and can be treated through degradation thereof via induction of autophagy by the subject invention. For example, such diseases include Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, x-linked spinobulbar muscular atrophy, and neuronal intranuclear hyaline inclusion disease. The diseases also include cancer e.g., any cancer wherein the induction of autophagy would inhibit cell growth and division, reduce mutagenesis, remove mitochondria and other organelles damaged by reactive oxygen species or kill developing tumor cells. They can be chronic diseases which refers to persistent and lasting diseases, medical conditions or diseases that have developed slowly. The diseases that can be treated by the subject invention also include, but not limited to, cardiovascular disorders, autoimmune disorders, metabolic disorders, hamartoma syndrome, genetic muscle disorders, and myopathies.

The term "autophagy inducing compound" refers to a compound that induces autophagy in a cell. The term autophagy inducing compound, as used herein, comprises the compound disclosed herein as well as the variants, isomers, metabolites or derivatives thereof.

The term "pharmaceutically acceptable carrier" refers to any carriers known to those skilled in the art to be suitable for a particular mode of administration. For example, carriers may include one or more solvents, dispersion media, diluents, adjuvants, excipients, vehicles, coatings, antibacterial and antifungal agents, isotonic and absorption delaying agents and the like, that are compatible with the compounds of the present invention. In addition, the compounds of formula (I-V) or salt and derivative thereof can be mixed with other active materials that do not impair the desired action, or with materials that supplement the desired action, or have another action. The autophagy inducing compounds may be formulated as the sole pharmaceutically active ingredient in the composition or may be combined with other active ingredients.

The phrase "therapeutically effective amount" refers to an amount of the compound of the present invention being sufficient to show benefit or clinical significance to an individual. Those skilled in the art would appreciate the actual amount or dose administered, and time-course of administration, will depend on the nature and severity of the diseases being treated, the age and general condition of the subject being treated as well as the mode of administration and so forth.

DETAILED DESCRIPTION OF THE INVENTION

The present invention pertains to therapeutic applications of synthesized analogues of compounds of formula (I-V):

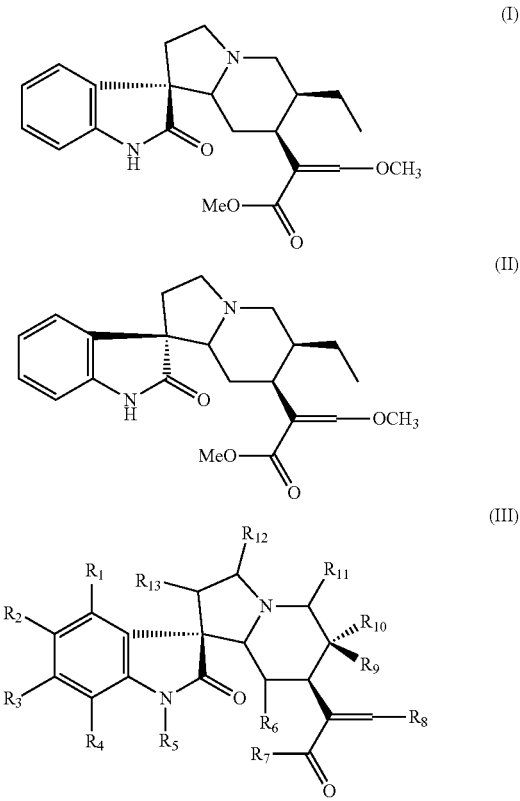

-continued

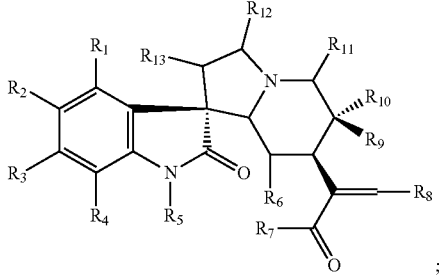

(IV)

which function as autophagy inducers. In particular, the synthetic analogues of compound of formula (I) are potent autophagy inducers in neuronal cells.

The present invention also provides methods and compositions useful for inducing autophagy that includes a therapeutically effective amount of the synthetic analogues of compound of formula (I), and a pharmaceutically acceptable salt thereof. The compound of formula (I) is also an mTOR-independent and beclin 1-dependent autophagy inducer that is capable of promoting maturation of autophagosome in autophagy for degrading abnormal proteins that are prone to aggregation. In one embodiment, the compound of the present invention and the composition containing the compound of the present invention are able to pass through blood brain barrier to induce autophagy, thereby degrading protein aggregates in cells/tissues of the nervous system. In this embodiment, the cells/tissues in the nervous system are selected from the group consisting of but are not limited to cortical neurons, hippocampus neurons, Thyrosine hydrolase positive neurons, glial cells. In one embodiment, the abnormal proteins that can be degraded by autophagy induced by the compound and composition of the present invention include but are not limited to α-syn, huntingtin, tau, SOD1, PMP22, ataxin, synphilin 1, and variants and mutated forms thereof and any other disease causing aggregate-prone proteins. In a preferred embodiment, the present invention is able to degrade wild-type and mutant forms of α-syn monomers, wild-type and mutant forms of α-syn oligomers and wild-type and mutant forms of α-syn and synphilin-1 aggresomes.

In one embodiment, the synthetic compounds of formula (I) are tetracyclic oxindole alkaloids, synthesized by chemistry method. In another embodiment, the synthesized compound of formula (I) is a synthetic analogue of Corynoxine B (Cory B).

In one embodiment, the diseases that can be treated by the compounds and composition of the present invention are those that can benefit from autophagy inducement. For example: aggregate-prone diseases that are caused by abnormal aggregation and/or deposition of aggregate-prone proteins, wherein the autophagy promotes the clearance of protein aggregation. These aggregate-prone diseases include but not limited to Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, x-linked spinobulbar muscular atrophy, and neuronal intranuclear hyaline inclusion disease.

In another embodiment, diseases also include cancer, wherein the induction of autophagy would inhibit abnormal cell growth and division, reduce mutagenesis, and remove mitochondria and other organelles damaged by reactive oxygen species or kill developing tumor cells. The cancer may include but not limited to cancer of the breast, liver, prostate, stomach, colon, GI tract, pancreases, skin, head, neck, throat, bladder, eye, esophagus, lung, kidney, or brain.

In yet another embodiment, diseases that benefit from autophagy can be chronic diseases which refer to a persistent and lasting disease, medical condition or one that has developed slowly. In yet another embodiment, the diseases also include cardiovascular disorders, autoimmune disorders, metabolic disorders, hamartoma syndrome, genetic muscle disorders, and myopathies. Examples of diseases that benefit from autophagy are disclosed in WO2010/129681 and US2010/0267704, the disclosures of which are incorporated herein by reference in their entirety. Moreover, infections wherein pathogens or pathogen proteins are degraded by autophagosomes and transferred to lysosomes for degradation are susceptible to treatment with autophagy inducer. For example tuberculosis, Group A Streptococcus infections, and viral infections (e.g., herpes simples virus type I) may be treated according to the present invention.

The compounds and the compositions of present invention may be administered alone or in combination with one or more other therapeutic agent(s) known to treat diseases that can benefit from autophagy, such as rapamycin; or a compound that may potentiate the autophagy inducing activity of the compounds of formula (I-IV). In some embodiments, where the treatment of disease is cancer, the present invention may be administered in conjunction with chemotherapeutic agents that are known in the art. Examples of chemotherapeutic agents that may be used in conjunction with the present invention are described in US2011/0014303, the disclosure of which is incorporated herein by reference in its entirety. Further, the compounds of the present invention can be affiliated with monoclonal antibodies to various cancer antigens or aggregate-prone proteins such that the autophagy-inducing properties are directed to cancer cells or cells where abnormal protein aggregation and/or deposition occur.

In another embodiment, the composition of the present invention additionally includes a pharmaceutically acceptable carrier, excipient, buffer, stabilizer or other materials known to those skilled in the art to be suitable for administration to living organisms. Such materials should be neither toxic, interfere with nor impair the efficacy of the compounds of the present invention. The materials may have another effect or supplement the autophagy inducing activity of the compounds of present invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of those skilled in the art.

The method of treatment for the diseases that benefit from autophagy of the present invention includes administering a therapeutically effective amount of the compounds of the present invention or the composition containing the compound of the present invention to a subject in need thereof, where the subject is an animal including a human. Methods of the present invention further include administering the one or more therapeutic agent(s) in conjunction with the compounds or the composition of the present invention. The mode of administration of the composition of the present invention includes topical, parenteral, intravenous, intraarterial, subcutaneous, intramuscular, intracranial, intraorbital, ophthalmical, intraventricular, intracapsular, intraspinal, intracisternal, intraperitoneal, intranasal, by aerosol, by suppositories, or by oral delivery. The compositions may be administered independently or in combination with other compositions if necessary. The compositions may also be prepared in different forms such as cream, gel, lotion, solution, solid, tablet, capsule, powder, paste, aerosol, etc depending on the desired modes of administration.

Additionally, it will be apparent to those of ordinary skill in the art that the course of treatment, such as, the number of doses of the composition given per day for a defined number of days will principally be determined by the nature and extent of the condition being treated, the form, route and site of administration, and the individual being treated. Suitable conditions can be determined by conventional techniques.

The present invention is further illustrated by the following working examples, which should not be construed as further limiting. While the working examples merely rely upon on the clearance of alpha-synuclein and its variants by Cory B and synthetic analogues of Cory B, the working examples are intended to demonstrate the autophagy induction ability to degrade aggregate-prone proteins, it is to be understood that other aggregate-prone proteins can also be cleared by the claimed invention.

EXAMPLES

In the following examples, the following materials are used; various commercial sources for the materials are provided. Details of the various protocols are also set forth below:

Reagents and antibodies Corynoxine B was purchased from Aktin Chemicals. 3-MA (M9281) and chloroquine (C6628) were purchased from Sigma-Aldrich. Rapamycin (R5000) was purchased from LC Laboratories. LysoTracker Red DND-99 (L-7528), goat anti-mouse (626520) and goat anti-rabbit (G21234) secondary antibodies were purchased from Invitrogen. Anti-β-actin (sc-47778), anti-GFP (sc-8334) and anti-tyrosine hydroxylase (sc-14007) antibodies were purchased from Santa Cruz Biotechnology. Anti-LC3 (2775), anti-phospho-mTOR (5536), anti-phospho-p70S6K (9234), anti-(3738) antibodies were purchased from Cell Signaling Technology. Anti-α-syn antibody (610786) was purchased from BD Transduction Laboratories. The instant Drosophila food (173212) was purchased from Carolina Biological Supply Company.

Cell lines and cell culture. N2a and SH-SY5Y cells were maintained in DMEM, supplemented with 10% FBS. PC12 cells were grown in DMEM (12800017, Invitrogen), supplemented with 10% FBS (10099141, Invitrogen) and 5% horse serum (16050122, Invitrogen). N2a cells constitutively expressing GFP-LC3 were selected using 800 µg/ml G418 (10131027, Invitrogen) and maintained in 200 µg/ml G418.

Primary neuron culture. The E17 embryonic pup brains were dissected and cortices were placed in a Petri dish containing ice cold EBSS, with meninges carefully removed. Tissues were digested in 5 ml of digestion solution (EBSS containing 0.5 mM EDTA (E6758, Sigma), 0.5 mg/ml Papain (3120, Worthington Biochem) and 4 mg/ml L-Cysteine (C7880, Sigma)) at 37° C. for 15 minutes. The tissue was sucked out in 1 ml of digestion solution and mixed with 3 ml of digestion inhibition solution (EBSS containing 5 mg/ml BSA (A2153, Sigma), 5 mg/ml Trypsin inhibitor (T9253, Sigma) and 10 µg/ml DNase (DN25, Sigma)). The mixed tissue solution was thoroughly mixed to dissociate the cells and then transferred to a 50 ml tube through a 70 µm filter. The cells were collected by centrifugation and re-suspended in seeding medium (DMEM containing 10% FBS and 10% horse serum). The cells were seeded on poly-D-lysine treated plates, at low density for imaging ($1 \times 10^5$ cells/well of 12-well plate), or at a high density for biochemistry analysis ($3 \times 10^6$ cells/well of 6-well plate). Four hours later, seeding medium was removed and replaced with neuorbasal medium (21103049, Invitrogen) supplemented with B-27 supplement (0080085SA, Invitrogen). Two days after culture, 5 µM Ara-C(C6645, Sigma) was added. Half of the medium was changed 24 hours later. Cultures were fed every 3 days by replacing half of the old media with fresh media. Cultures were maintained for at least one week for neuron maturation.

Differentiation of stem cells into dopaminergic neurons. The human embryonic stem (ES) cells were differentiated into dopaminergic neurons according to a previously described protocol with minor changes. Initially, ES cells were digested with dispase (17105041, Invitrogen,) and broken into smaller clusters to form the embryonic bodies. The next day, undifferentiated floating ES cell aggregates were transferred to a new flask. The cells were maintained in DMEM/F12 medium (11320082, Invitrogen) with half medium changed every day for 3 days. On the fourth day, ES cell aggregates were collected by centrifuge and re-suspended in NSM (DMEM/F12 containing 1% N2 supplement (17502048, Invitrogen), 1 µg/ml Heparin (H3149, Sigma), 200 µM NEAA (11140050, Invitrogen) and 2 mM L-glutamine (25030081, Invitrogen)) supplemented with 10% FBS. Embryonic stem cells were transferred to a new flask and medium was changed every other day. Three days later, cell aggregates were transferred to 6-well-plates. The next day, the FBS containing media were replaced with NSM containing 20 ng/ml FGF8 (PHG0184, Invitrogen) and 100 ng/ml SHH (PMC2095, Invitrogen), media were changed every other day. Five days later, the colonies in the dish were detached by pipetting gently with a P1000 pipette. Cells were collected by centrifugation and resuspended in NSM containing 50 ng/ml FGF8, 100 ng/ml SHH, 2% B27, 200 µM NEAA and transferred to a new flask. Media were changed every other day. Six days later, neurospheres were collected and digested in 200 µl accutase (A1110501, Invitrogen)/trypsin (25300062, Invitrogen) (1:1) for 3 minutes. Digestion was stopped by adding 200 µl trypsin inhibitor (R007100, Invitrogen) and cells were re-suspended in NDM (Neurobasal medium containing 1% N2 supplement and 2% B27 supplement (17504044, Invitrogen)) and plated onto laminin (23017015, Invitrogen) coated cover slips. The next day, 1 ml NDM supplemented with 20 ng/ml BDNF (10908010, Invitrogen), 50 ng/ml GDNF (PHC7045, Invitrogen), 50 ng/ml FGF8, 100 ng/ml SHH, 2% B27, 200 µM AA, 1 µM cAMP (A9501, Sigma), 1 µg/ml laminin and 1 ng/ml TGFβ3 (PHG9305, Invitrogen) was added to each well and media were changed every other day for 10 days. Successful differentiation of dopaminergic neurons was confirmed by tyrosine hydroxylase staining.

Plasmids and transfection. TfLC3 plasmids were a generous gift from Dr. T. Yoshimori (Osaka University, Japan). GNS and SGC plasmids were donated by Dr. Pamela J. McLean (Harvard Medical School, U.S.A.). Cells were transfected with plasmids using lipofectamine 2000 (11668019, Invitrogen) according to the manufacturer's protocol.

Native and denatured PAGE and Western blotting analysis. Samples to be run under denaturing conditions were lysed with RIPA lysis buffer (150 mM NaCl, 50 mM Tris-HCl, 0.35% sodium deoxycholate, 1 mM EDTA, 1% NP40, 1 mM PMSF, 5 μg/ml aprotinin, 5 μg/ml leupeptin). Samples for native gels were lysed with detergent-free lysis buffer (50 mM Tris/HCl pH 7.4, 175 mM NaCl, 5 mM EDTA pH 8.0, 1 mM PMSF, 5 μg/ml aprotinin, 5 μg/ml leupeptin), and sheared 5 times through a 28-gauge needle followed by 2 times of sonication for 5 seconds according to previously described protocol. For denaturing, SDS-PAGE was performed using Tris-Glycine SDS running buffer and SDS sample buffer, and for native conditions, native-PAGE was run with detergent-free Tris-Glycine running buffer (BN2007, Invitrogen) and 4x native sample buffer (BN2003, Invitrogen) on a pre-casted native PAGE gel (BN1002BOX, Invitrogen). The proteins on the gels were then transferred to PVDF membrane (RPN303F, GE Healthcare) and processed for immunoblotting. Membranes were blocked with 5% non-fat milk and probed with the appropriate primary and secondary antibodies. The desired bands were visualized using the ECL kit (32106, Pierce). The band density was quantified using the ImageJ program and normalized to that of the control group.

Immunostaining. Cells were fixed with 3.7% paraformaldehyde in PBS, immunolabeled with antibody against TH (2792, Cell Signaling Technology) or HA (2367, Cell Signaling Technology) and fluorophore-conjugated secondary antibody (Cy3-conjugated goat anti-rabbit (078-15-061, KPL) or Cy5-conjugated goat anti-mouse (072-15-18-18, KPL)), and mounted with FluorSave reagent (345789, Calbiochem). Fluorescence was recorded using a confocal microscope.

Cell imaging and puncta counting. Cells were fixed in 3.7% paraformaldehyde (158127, Sigma) for 10 minutes and mounted with FluorSave reagent. Cell images were recorded using a fluorescence microscope or confocal microscope. GFP or RFP Puncta number were counted in cells as described previously. Briefly, the GFP-LC3 or RFP-LC3 puncta in each cell were manually counted, and at least 50 cells were randomly selected for counting in each group. The data presented were from one representative experiment of at least 3 independent experiments.

Drosophila culture and drug feeding. Flies were raised at 25° C. on standard corn meal medium supplemented with dry yeast. Cory B and rapamycin were initially dissolved in DMSO then diluted in water to desired concentrations. The drug containing water was added into instant Drosophila food and mixed thoroughly. As the control, the same amount of DMSO was also mixed with instant Drosophila food. For the treatment, L3 larvae or adult flies were transferred to the drug-containing medium and incubated for indicated time.

Lysotracker staining and quantitative analysis of autophagic structures. L3 larvae were dissected using fine forceps under a dissecting microscope and inverted so that fat bodies were exposed to the incubating solution. The larvae carcasses were stained with 100 nM of LysoTracker red in PBS for 5 minutes at room temperature. After the incubation, the larvae carcasses were rinsed once in PBS and transferred to a glass slide with a drop of mounting medium on it. The fat bodies (one major lobe per animal) were excised, and the remaining tissue was discarded. Fat body lobes were then covered with a cover slide and immediately observed under a standard fluorescence microscope. Quantitative analysis of lysotracker-positive spots was performed according to previous described protocol with minor revision. At least 6 fat body lobes from three independent animals of each group were obtained. The numbers of lysotracker-positive spots were quantified from at least 20 randomly selected fluorescent image fields (4700 μm$^2$/field).

Example I

Cory B Induces Autophagy in Neuronal Cell Lines

Figure 1B:
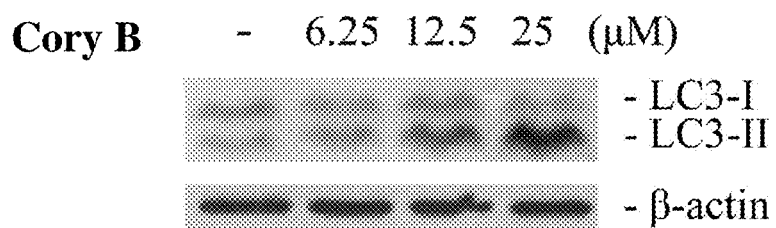
Figure 1C:
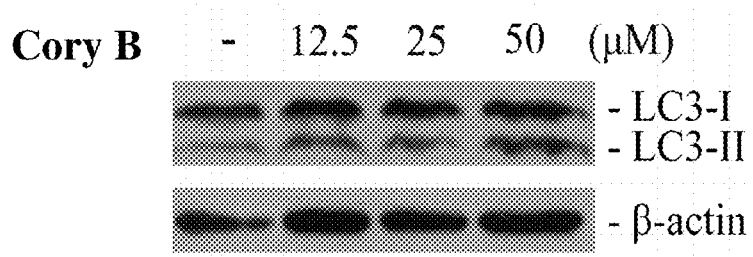
Figure 1D:
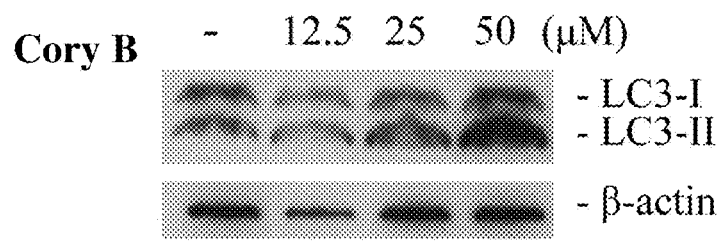

Induction of autophagy has been shown to be more difficult in neuronal cells than in non-neuronal cells. In order to confirm the neuronal autophagy inducing activity of Cory B (its chemical structure is shown in FIG. 1A), mouse neuroblastoma N2a, rat phenochromocytoma PC12 and human neurobastoma SH-SY5Y are treated with different concentrations of Cory B for 24 hours and cell lysates are subjected to western blotting analysis of LC3-II expression which is an autophagy-specific marker. It is shown that Cory B increases levels of LC3-II in N2a, PC12 and SH-SY5Y cells in a dose-dependent manner, without affecting LC3-I levels (FIG. 1B-D).

Figure 1E:
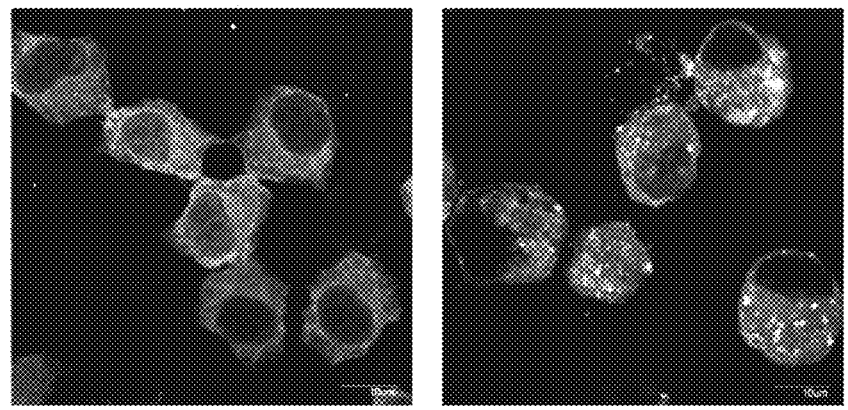
Figure 1F:
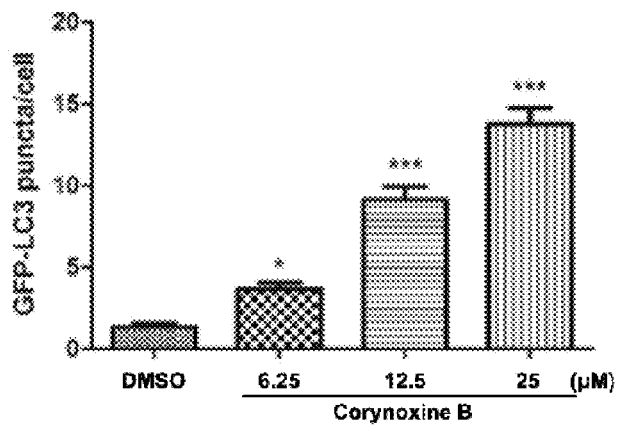

Further, a neuroblastoma cell line N2a constantly expressing GFP-LC3 (a standard autophagy marker protein) is established. The formation of GFP-LC3 puncta under Cory B treatment is observed under a confocal microscope. Data is presented as the mean±SEM of one representative experiment from three independent experiments. (*p<0.05, ***p<0.001, one-way ANOVA for multiple comparison and Tukey's test as post hoc test). The data illustrates that Cory B induces massive GFP-LC3 puncta formation in the N2a GFP-LC3 cells (FIG. 1E).

The elevated levels of LC3-II expression in various neuronal cell lines and massive GFP-LC3 puncta formation in N2a cells in the presence of CORY B demonstrate that CORY B is a potent autophagy inducer in neurons.

Figure 2A:
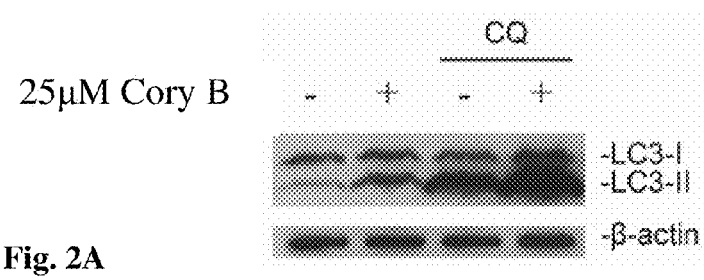
FIG. 2: Western blot analysis of the expression level of autophagy marker, LC3-II, in N2a cells induced by 25 μM Cory B and/or 30 μM lysosome inhibitor chloroquine (CQ) for 12 hours (FIG. 2A), and the ratio of LC3-II expression to beta-actin in different treatment groups (FIG. 2B); fluorescent images of GFP signal (FIG. 2C) and number of GFP-LC3 puncta per cell (FIG. 2D) in different treatment groups including 5 mM 3-MA, 30 μM CQ, and/or 25 μM Cory B for 24 hours; double fluorescent images of GFP and/or RFP signals from N2a cells containing a tandem fluorescent mRFT-GFP-LC3 (Tf-LC3) construct (FIG. 2E) and number of GFP-LC3 and RFP-LC3 puncta per cell in different treatment groups (FIG. 2F) including 25 μM Cory B and/or 30 μM CQ for 24 hours.
Figure 2B:
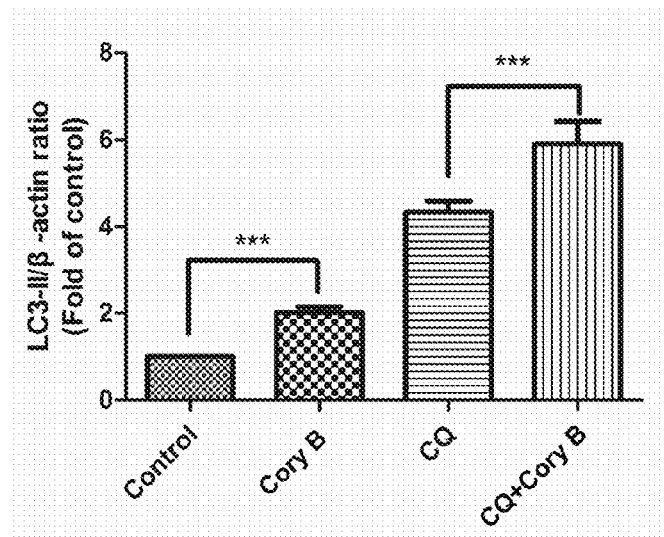
Figure 2C:
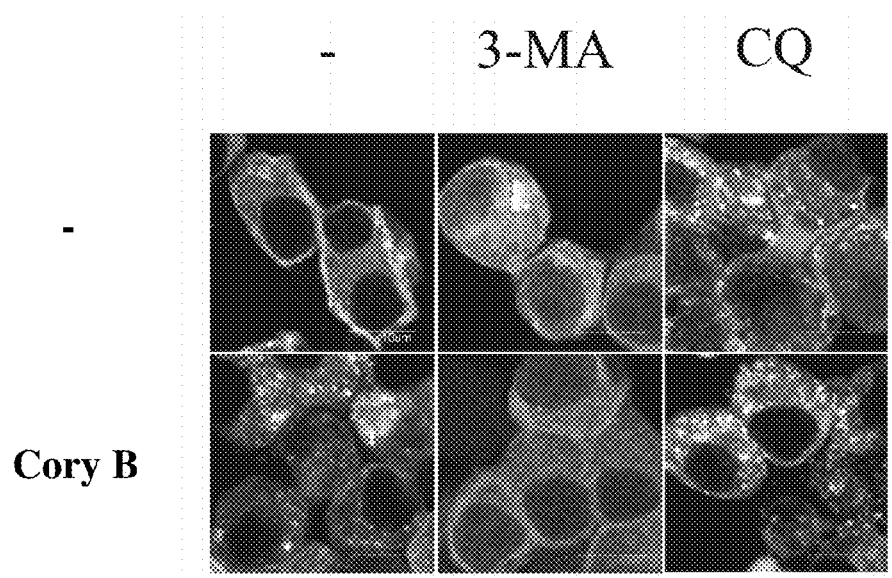
Figure 2D:
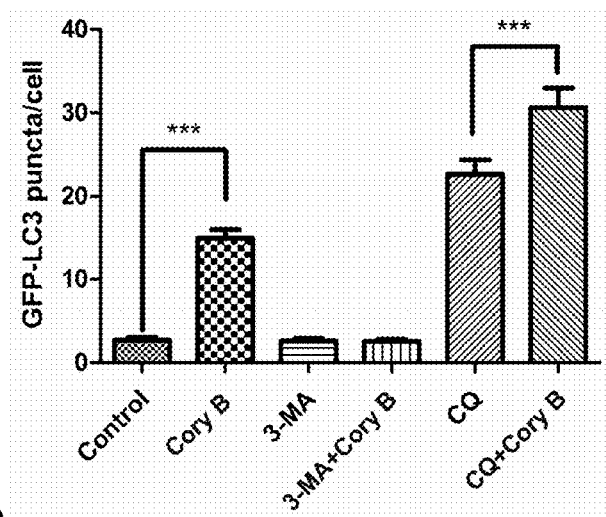

To confirm that enhancement of autophagy markers by Cory B is due to induction of autophagy rather than blockage of autophagosome maturation, N2a cells are treated with 25 μM Cory B or 30 μM lysosome inhibitor CQ together with Cory B for 12 hours. Cell lysates are subject to western blot analysis. Data are presented as the mean±SEM from 3 independent experiments (*p<0.001, one-way ANOVA for multiple comparison and Tukey's test as post hoc test). Both LC3-II levels and the number of GFP-LC3 puncta in the Cory B and CQ co-treatment group are much higher than in the CQ-alone treatment group (FIG. 2A-D). Meanwhile, Cory B induces GFP-LC3 puncta formation is abolished by treatment of 5 mM autophagy inhibitor 3-MA for 24 hours (FIG. 2C, D). Cells were fixed in 4% paraformaldehyde and analyzed under a confocal microscope. Data are presented as the mean±SEM of one representative experiment from three independent experiments. (*p<0.001, one-way ANOVA for multiple comparison and Tukey's test as post hoc test). The abolishment of GFP-LC3 puncta formation by 3-MA suggests that the enhancement of LC3-II and GFP-LC3 puncta formation by Cory B is due to its ability to induce autophagy. Thus, Cory B is indeed an autophagy inducer in neuronal cells.

Figure 2E:
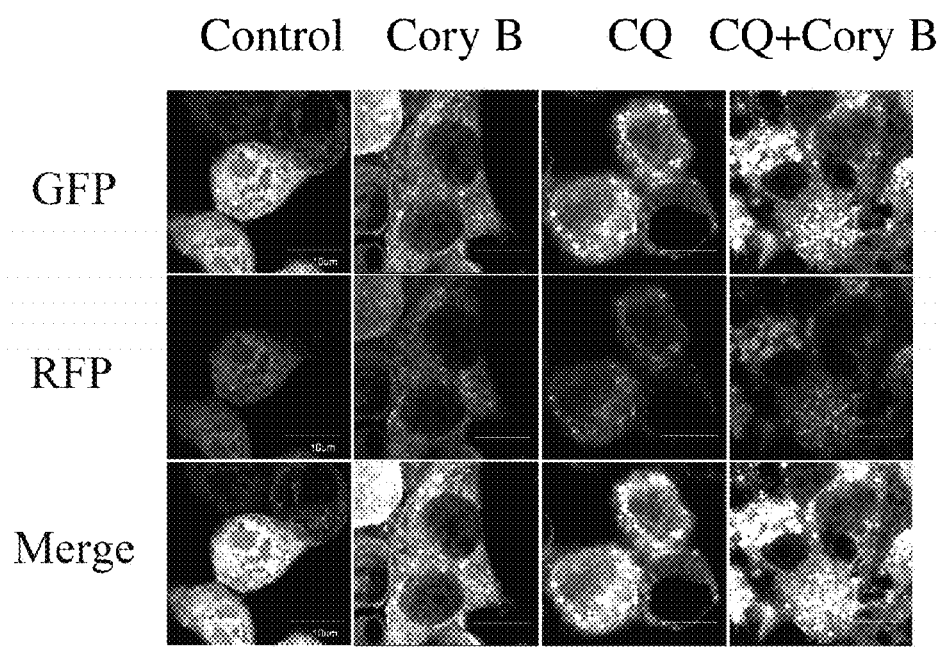
Figure 2F:
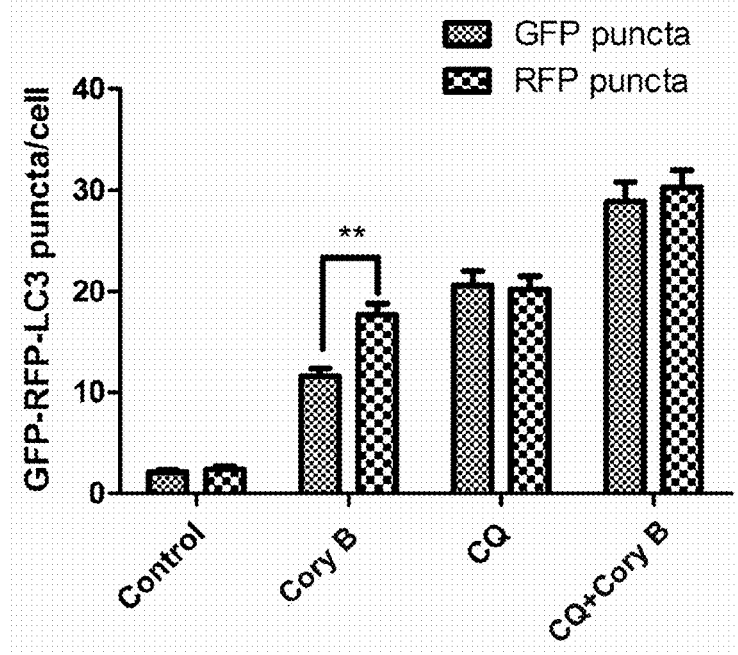

A system established by Kimura et al. based on a tandem fluorescent mRFP-GFP-LC3 (Tf-LC3) construct is used to investigate the autophagosome maturation process. mRFP is more stable than GFP in the acidic/proteolytic condition in lysosome. Therefore, red-only puncta indicates the normal maturation of the autolysosomes. In contrast, co-localization of GFP and RFP puncta indicates impaired fusion between autophagosomes and lysosomes or disruption of lysosome function. Here, this system is utilized and establishes a pattern of GFP and mRFP fluorescence changes in N2a cells after Cory B treatment. Cells are fixed in 4% paraformaldehyde and analyzed under a confocal microscope. Cory B induces massive GFP and mRFP puncta formation after 24 hours of Cory B treatment. However, the number of GFP puncta is much lower as compared to mRFP puncta, indicating efficient autophagosome-lysosome maturation and degradation. In cells treated with CQ, there is similar accumulation of GFP and mRFP puncta due to lysosome inhibition. In cells treated with both CQ and Cory B, the number of GFP and mRFP puncta are even more than in the CQ-alone group, but GFP and mRFP puncta numbers are very similar (FIG. 2E, F). The observations further confirm that enhancement of GFP- and RFP-LC3-II puncta expression by Cory B are achieved via autophagy induction flux in neuronal cells rather than inhibiting lysosomal degradation of LC3-II. Results were presented as means±SEM of one representative experiment from three independent repeats (**$p<0.01$ compare the difference between GFP and RFP puncta in each group, two-way ANOVA for multiple comparison and Bonferroni test as post hoc test).

Example II

Cory B Induces Autophagy in Primary Mouse Cortical Neurons

To further confirm the pro-autophagic effect of Cory B on primary neurons, mouse primary cortical neurons isolated from E17 embryonic ICR mice are used in this study. The primary neurons are treated with different concentrations of Cory B for 24 hours, and autophagic marker GFP-LC3 expression is examined by Western blotting analysis. Neurons are fixed in 4% paraformaldehyde and analyzed under a confocal microscope. GFP-LC3 puncta number in each GFP positive neuron is counted and at least 20 neurons in each group is counted. Data presents as the mean±SEM of one representative experiment from three independent experiments (***$p<0.001$, Student t test).

Figure 3A:
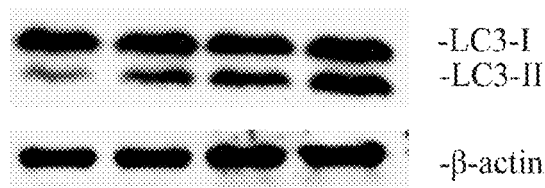
FIG. 3: Western blot shows the expression level of autophagy marker, LC3-II, in primary mouse cortical neuron isolated from E17 embryonic mice and induced by 0-50 μM Cory B (FIG. 3A); fluorescent images of GFP signal (FIG. 3B) and number of GFP-LC3 puncta per cell (FIG. 3C) in mouse embryonic primary cortical neuronal cell induced by 50 μM Cory B for 24 hours.
Figure 3B:
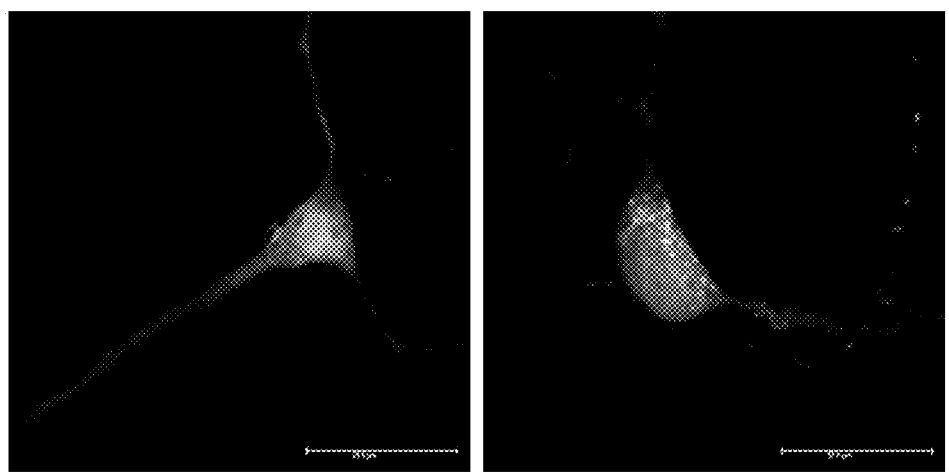
Figure 3C:
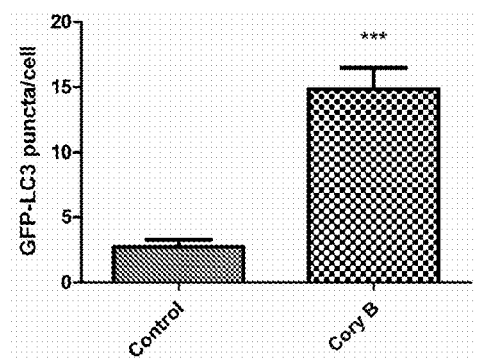

Again, a dose-dependent increase of LC3-II by Cory B is observed in mouse primary cortical neurons (FIG. 3A). In neurons transfected with the GFP-LC3 construct, Cory B induces massive formation of GFP puncta (FIGS. 3B, C). These data indicate that Cory B is also a potent autophagy inducer in primary neurons.

Example III

Cory B Induces Autophagy In Vivo

Figure 4A:
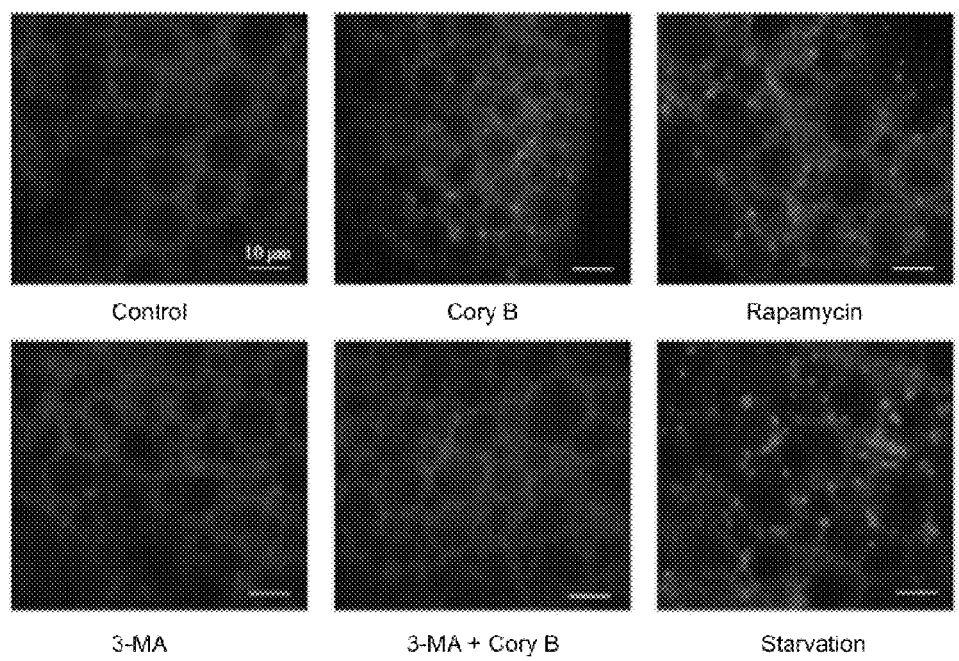
FIG. 4: Fluorescent images of LysoTracker red staining of L3 *Drosophila* larvae fat body in different treatment groups for 6 hours (FIG. 4A); number of LysoTracker red-positive spots per field in different treatment groups (FIG. 4B).
Figure 4B:
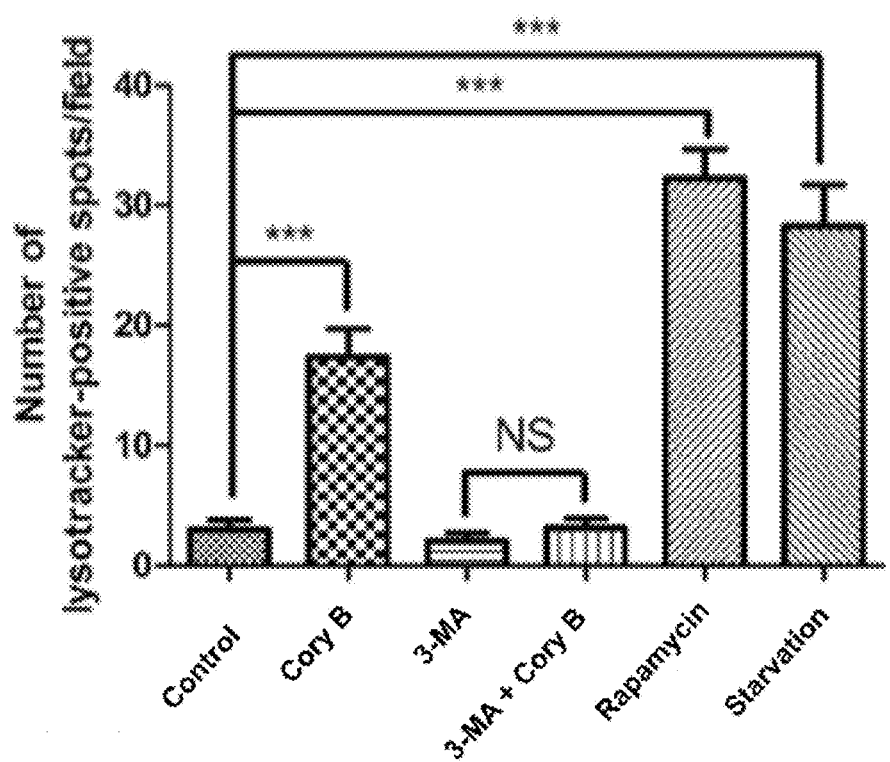

As the major nutrient storage organ of the larvae, the fat body is naturally sensitive to nutrient starvation and elicits a robust autophagic burst upon autophagic stimuli. The basal level of lysosomal activity under nutrient-sufficient conditions is low in fat bodies; however, expansion and acidification of the autolysosome in response to autophagy induction in the fat body can be visualized using the lysotropic dye LysoTracker Red. After 96 hours of egg laying, L3 Drosophila larvae are collected and fed with 0.2 mg/ml of Cory B for 6 hours, and fat bodies are then isolated for LysoTracker Red staining. As a positive control, L3 larvae are either fed with 5 µM of rapamycin for 24 hours or starved for 3 hours to induce autophagy. Cory B induces formation of LysoTracker Red-positive puncta in the L3 larvae fat bodies, in a similar pattern to rapamycin treatment or starvation (FIG. 4). Furthermore, Cory B-induces puncta formation is blocked by autophagy inhibitor 3-MA. These data illustrate that Cory B induces autophagy in fat bodies of Drosophila L3 larvae. Accordingly, Cory B behaves as a potent autophagy inducer both in vitro and in vivo. Data presents as the mean±SEM of one representative experiment from three independent experiments. (***$p<0.001$, one-way ANOVA for multiple comparison and Tukey's test as post hoc test).

Example IV

Figure 5A:
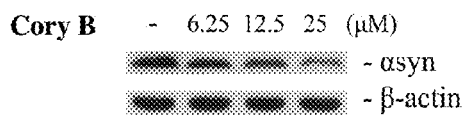
FIG. 5: Western blot analysis of expression level of WT α-syn (FIG. 5A), mutants α-syn A30T (FIG. 5B) and A53P (FIG. 5C), GFP control (FIG. 5D) WT α-syn in N2a cells with treatment of 25 μM Cory B or 5 mM 3-MA and 30 μM CQ (FIG. 5E) and the expression level of WT α-syn as compared to control in different treatment groups (FIG. 5F); schematic diagram of a bimolecular fluorescence complementation-based cell model for visualizing the degradation of α-syn oligomer by Cory B (FIG. 5G), and comparison in GFP signal in different treatment groups (FIG. 5H); western blot analysis of high molecular weight α-syn oligomer species (FIG. 5I); fluorescent images of co-expressed α-syn oligomer- and synphilin-1-GFP signal in N2a cells (FIG. 5J) and percentage of cells with GFP signal which is proportional to the percentage of aggresome formation (FIG. 5K) in different treatment groups.
Figure 5B:
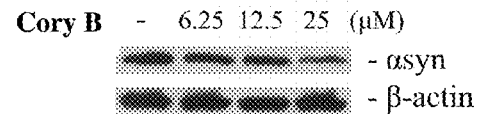
Figure 5C:
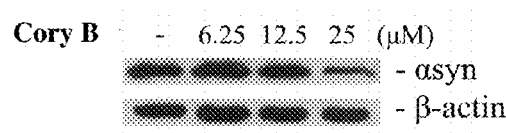
Figure 5D:
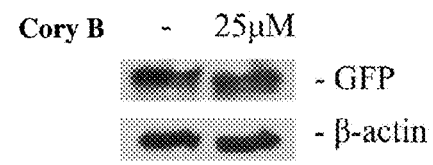
Figure 5E:
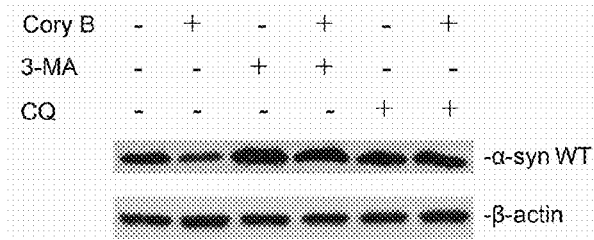
Figure 5F:
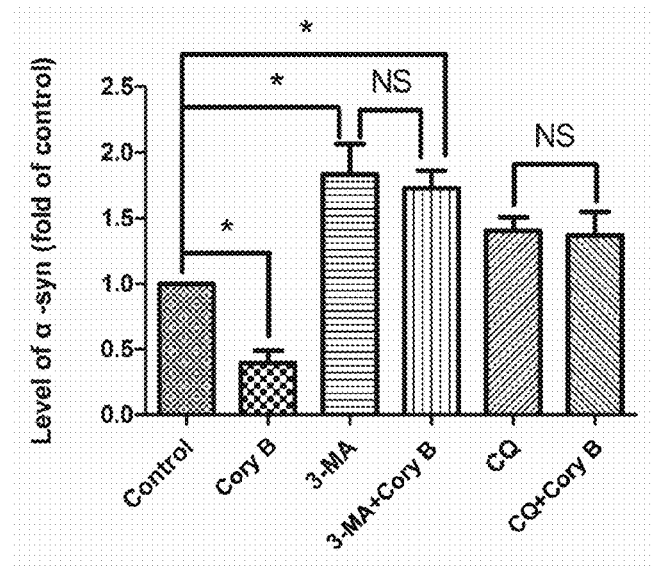

Cory B Promotes Clearance of Transiently Over-Expressed Pathogenic α-Syn Species in N2a Cells Via Autophagy Induction Autophagy has been suggested as a promising therapeutic strategy against synucleinopathies by promoting the clearance of α-syn. Cory B induced autophagy-dependent clearance of α-syn is examined in three different cellular models. N2a cells over-expressed in WT and α-syn mutants (A53T and A30P) and N2a cells with GFP as negative control are subjected to Cory B treatment for 24 hours. Cory B reduces WT and mutant α-syn levels in a dose-dependent manner (FIG. 5A-C), but does not reduce GFP levels (FIG. 5D). Clearance of α-syn induced by Cory B is confirmed to be dependent on the autophagy-lysosome pathway because 5 mM autophagy inhibitor 3-MA and 30 µM CQ treatments abolish pro-clearance activity of Cory B (FIG. 5E, F). Data presents as the mean±SEM from 3 independent experiments (*$p<0.05$, one-way ANOVA for multiple comparison and Tukey's test as post hoc test).

Figure 5G:
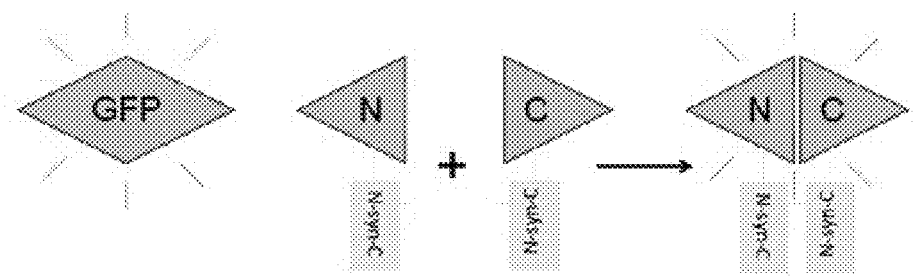
Figure 5H:
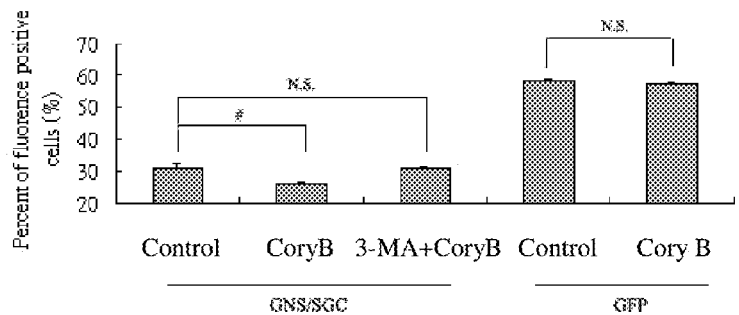
Figure 5I:
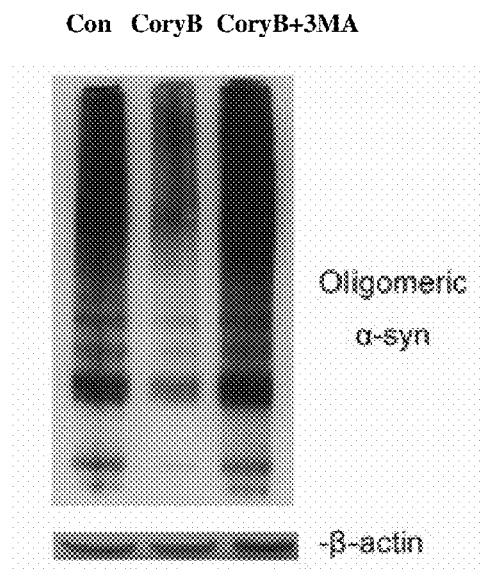
Figure 5J:
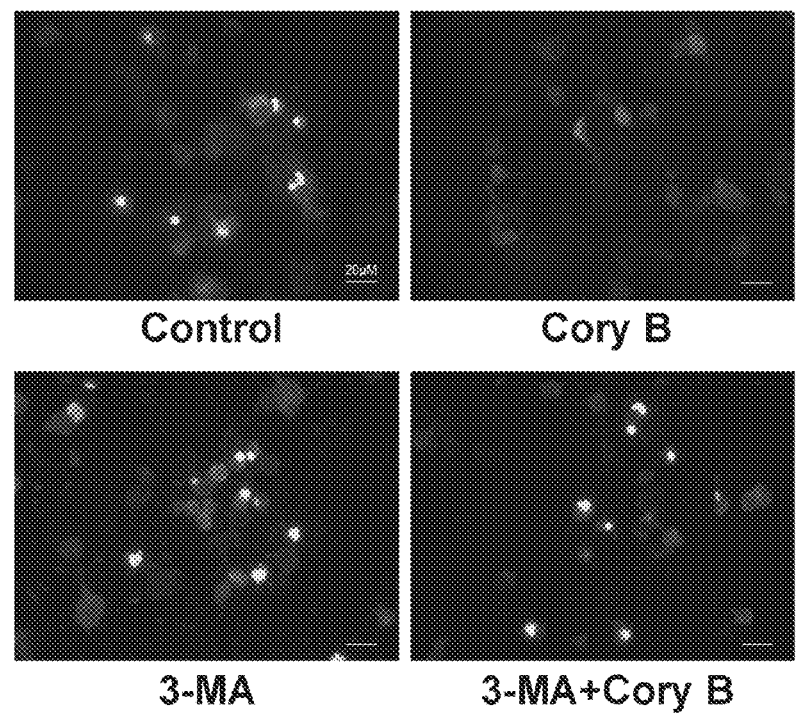
Figure 5K:
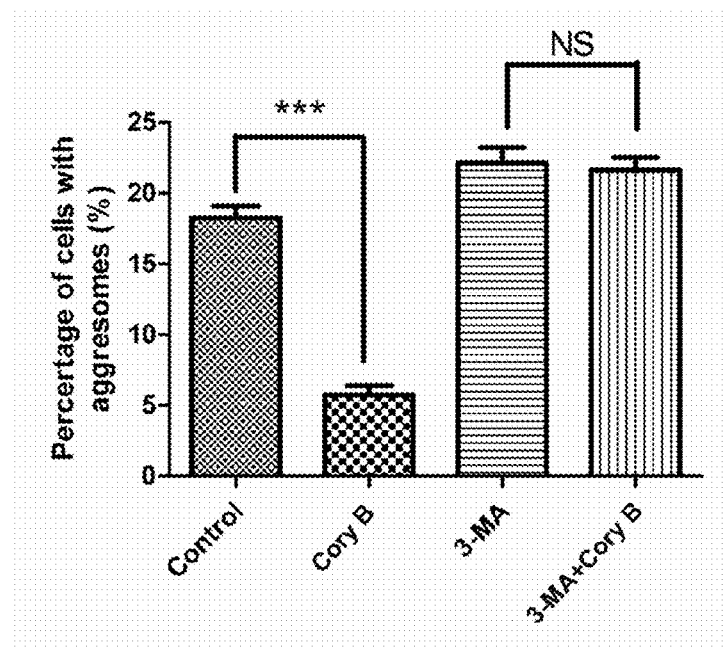

Second, the effect of Cory B on α-syn oligomers clearance is tested using a bimolecular fluorescence complementation (BiFC)-based cell model which enables visualization of α-syn oligomers. Two non-fluorescent fragments of GFP, GFP-N terminal fraction and GFP-C terminal fraction, are fused with α-syn protein; interaction of the two fragments reconstitutes the fluorophore (FIG. 5G). The presence of fluorescence signal indicates the formation of α-syn oligomers within cells. Mock transfected cells are used as blanks to gate the fluorescence-positive cells and signals stronger than $10^1$ RFU are considered as positive α-syn oligomers formation. Cells are treated with 25 µM Cory B and/or 5 mM 3-MA for 24 hours and harvested for flow cytometry analysis. Cory B promotes degradation of α-syn oligomers as illustrated by decreased fluorescence intensity (FIG. 5H, I) and percentage of cells having high molecular weight α-syn species (FIG. 5J), whereas this effect is prevented by 3-MA Data presents as the mean±SEM from 3 independent experiments (***$p<0.001$, one-way ANOVA for multiple comparison and Tukey's test as post hoc test).

α-syn and synphilin-1 are co-expressed in N2a cells to mimic aggresome formation and are treated with 25 µM Cory B or 5 mM 3-MA for 48 hours. Cells are fixed in 4% paraformaldehyde and analyzed under a fluorescence microscope. Cory B dramatically decreases the number of α-syn/ synphilin-1 aggresomes as seen in the dramatic decrease of fluorescence intensity observed in the Cory B treatment (FIG. 5K, L). The inhibition of Cory B clearance of various forms of α-syn and α-syn/synphilin-1 aggresomes in the presence of 3-MA further validates that such clearance is via the autophagy pathway. Data are presented as the mean±SEM from 3 independent experiments (***$p<0.001$, one-way ANOVA for multiple comparison and Tukey's test as post hoc test).

The results of Example IV shows that autophagy induced by Cory B is capable of degrading both the WT and mutated forms of α-syn as well as syn/synphilin-1 aggresomes in neuronal cells, and hence Cory B usefulness in treating aggregate-prone disorders.

Example V

Figure 6A:
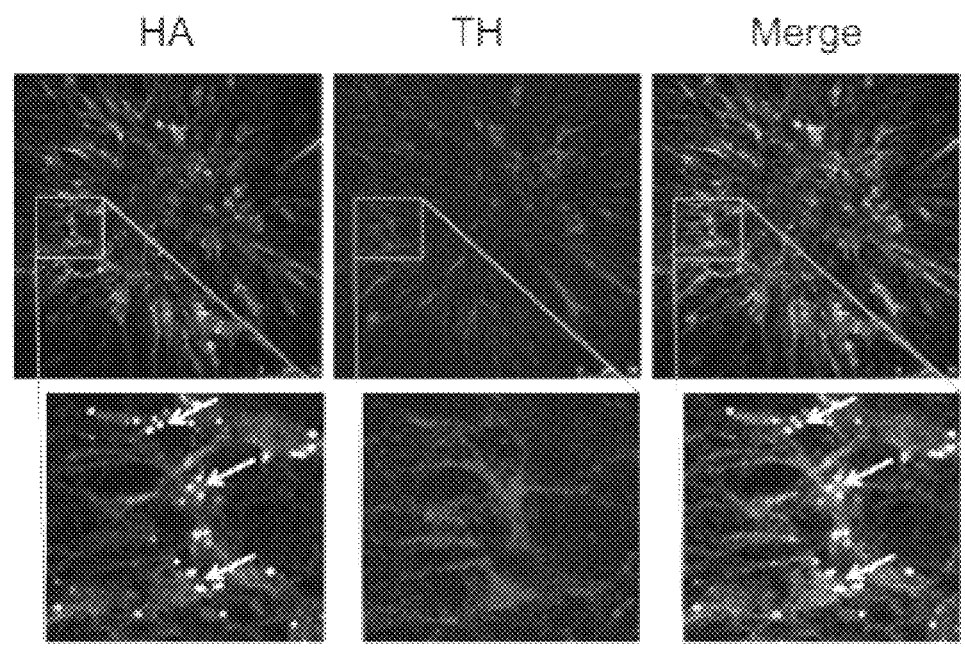
FIG. 6: Double fluorescent images of HA-staining for α-syn expression and tyrosine hydroxylase (TH) staining of human DA neurons differentiated from embryonic stem cells (FIG. 6A); western blot analysis of both WT and A53T α-syn expression levels in differentiated DA neurons (FIG. 6B).
Figure 6B:
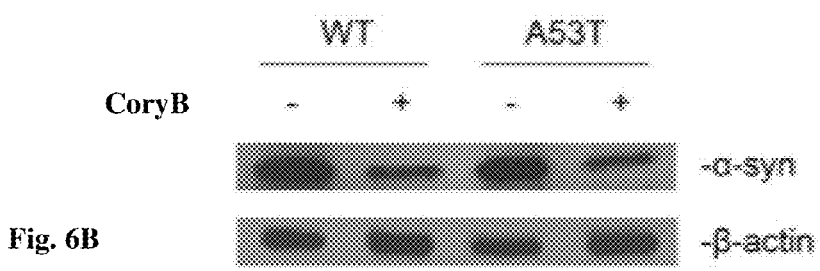

Cory B Promotes the Degradation of α-Syn in Human Dopaminergic Neurons Differentiated from Embryonic Stem Cells Dopaminergic neurons are the most affected cells in the brains of PD patients, and over-expression of α-syn in the central nervous system leads to dopaminergic neuron degeneration in multiple organisms from mice to C. elegans. Cory B promotes α-syn protein degradation via inducing autophagy in N2a cells transiently over-expressing α-syn is shown in FIG. 5. Human embryonic stem cell lines that constitutively express WT and A53T α-syn-HA are established by introducing respective plasmids using lentivirus. The stem cells are then differentiated into DA neurons. The differentiated DA neurons are confirmed by tyrosine hydroxylase (TH) staining, and expression of α-syn is confirmed by HA staining. The massive particles in HA staining images are typical α-syn aggregates (FIG. 6A). The white arrow indicates α-syn aggregates in the cells. As expected, Cory B treatment dramatically decreases both WT and A53T α-syn levels in differentiated DA neurons (FIG. 6B). Autophagy promoted by Cory B degrades α-syn and mutant thereof in human DA neurons where α-syn is accumulated in PD patients.

Example VI

Figure 7A:
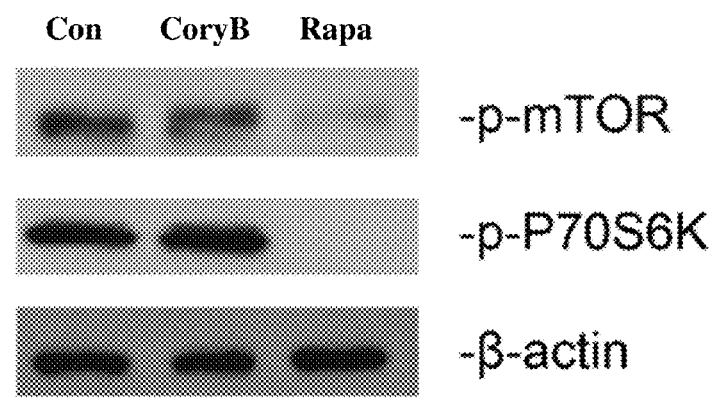
FIG. 7: Western blot analysis of expression level of phosphorylated mTOR (p-mTOR) or its substrate P70S6K (p-P70S6K) in N2a cells with treatment of 25 μM Cory B or 0.2 μM rapamycin for 6 hours (FIG. 7A); western blot analysis of Beclin 1 expression in N2a cells with non-target or Beclin 1-specific siRNA treatments followed by Cory B (FIG. 7B)
Figure 7B:
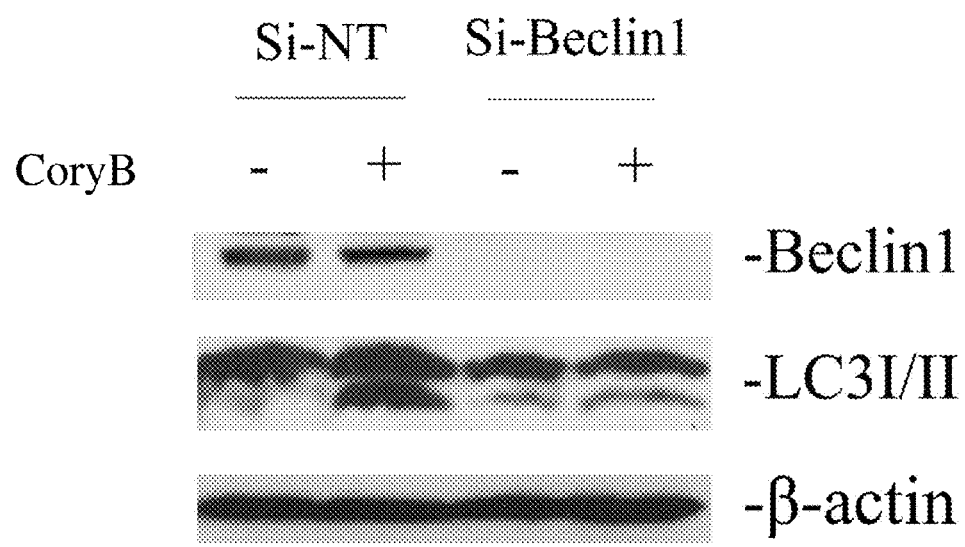

Cory B Induces Autophagy in Neuronal Cells in an mTOR-Independent but Beclin-1-Dependent Manner To elucidate the molecular mechanism of Cory B action, the classic autophagy controlling pathway, the mTOR pathway is first examined. However, neither phosphorylated mTOR nor its substrate P70S6K are affected by Cory B treatment, although phosphorylated mTOR and pP70S6K were dramatically inhibited by rapamycin (FIG. 7A). Several other pathways reported to be involved in the activation of autophagy, including AKT, AMPK, MEK/ERK, JNK, and ER stress pathways, and calcium signaling pathway (data not shown), are also tested. However, none of the above mentioned pathways are altered by Cory B treatment. Beclin-1 is a key player in the activation of autophagy, and up-regulated Beclin-1 has been shown to directly induce autophagy. To understand the role of Beclin-1 in Cory B-induced autophagy in neuronal cells, the effect of Cory B in the presence or absence of Beclin-1 depletion by RNA interference is examined. Data reveals that Cory B does not affect the expression of Beclin-1, but Beclin-1 siRNA treatment completely blocks Cory B-induced autophagy (FIG. 7B). These data indicate that Cory B induces autophagy in neuronal cells in an mTOR-independent but Beclin-1-dependent manner.

Example VII

Different Activity of Tetracyclic Oxindole Alkaloids on Autophagy Indution

Figure 8A:
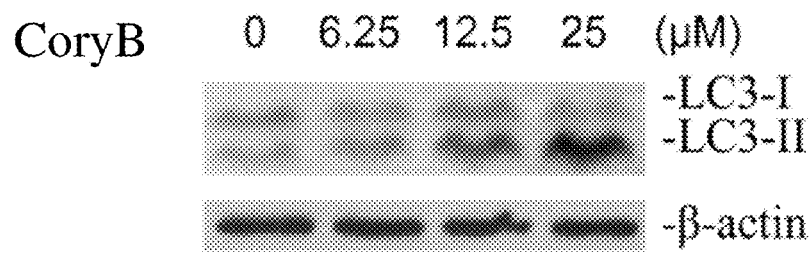
FIG. 8: Western blot analysis of the LC3II expression level in N2a cells treated with different oxindole alkaloids; Corynoxine B (Cory B) (FIG. 8A), Corynoxine (Cory) (FIG. 8B) Rhynchophylline (Rhy) (FIG. 8C) and IsoRhynchophylline (IsoRhy) (FIG. 8D) for 12 hours.
Figure 8B:
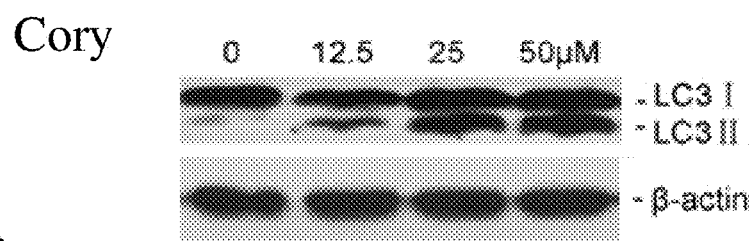
Figure 8C:
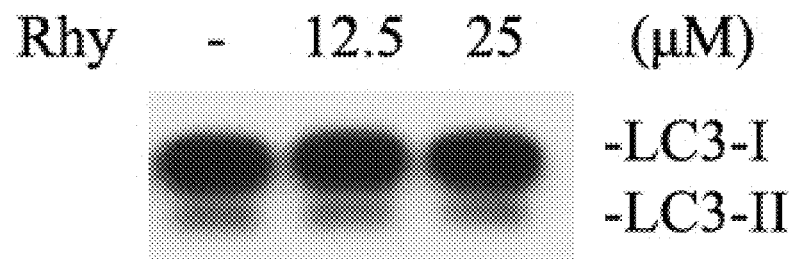
Figure 8D:
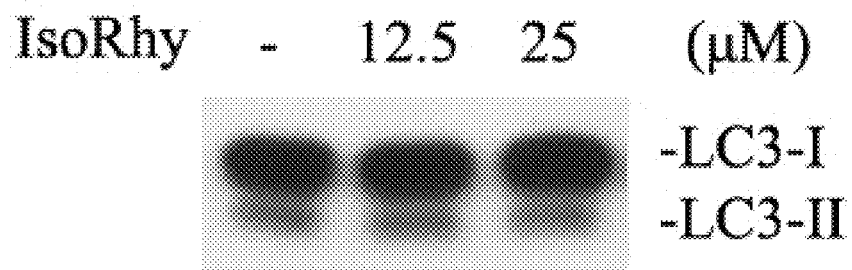

To compare the activities of oxindole alkaloids on autophagy induction, LC3II expression levels in N2a cells after treatment with Corynoxine B (Cory B) (FIG. 8A), Corynoxine (Cory) (FIG. 8B), Rhynchophylline (Rhy) (FIG. 8C) and Isorhynchophylline (IsoRhy) for 12 hours are examined. The data reveals that Cory B and Cory significantly activate autophagy in N2a cells, while Rhy and IsoRhy did not show any activity on autophagy induction.

Example VIII

Protective Role of CoryB and Cory on the In Vitro and In Vivo AD Models

Figure 9A:
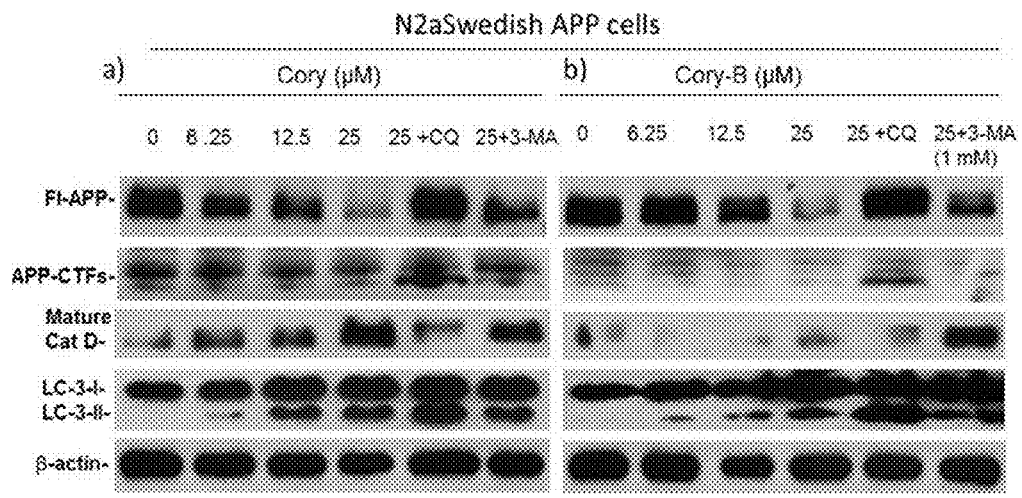
FIG. 9: Protective role of CoryB and Cory on the in vitro and in vivo AD models. Western blot analysis of LC3, full length and CTF APP (FIG. 9A, FIG. 9B). Immunostaining and Western blot analysis of tau and APP level in the JNPL P301 Tau mice and Tg2567 APP mice (FIG. 9C, FIG. 9D).
Figure 9B:
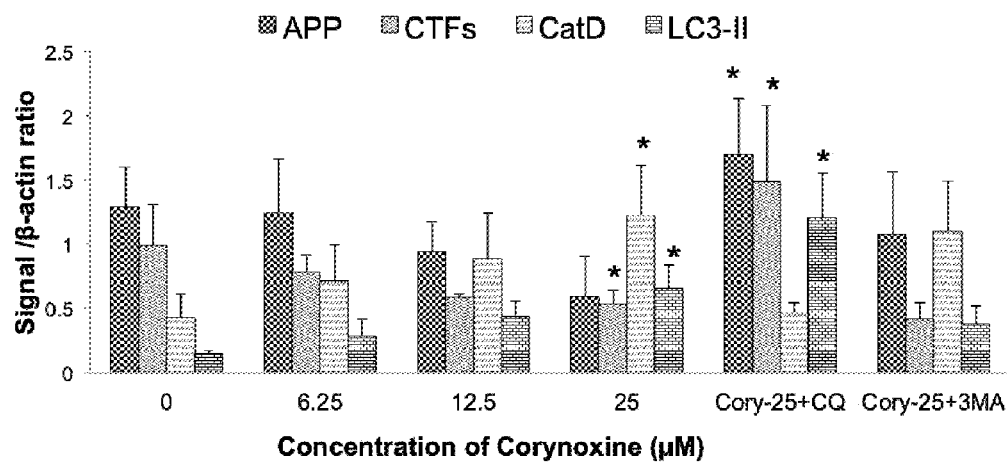
Figure 9C:
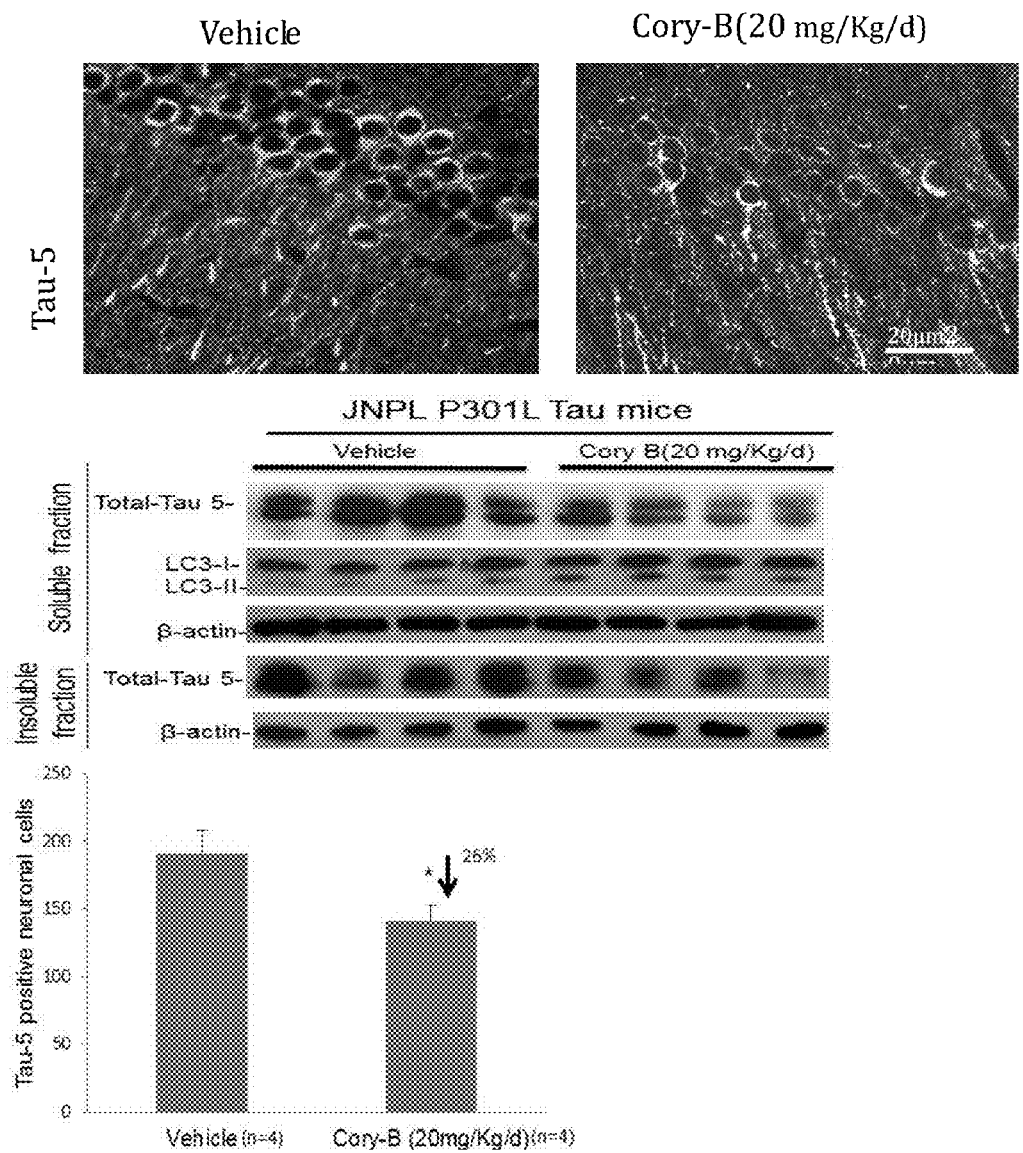
Figure 9D:
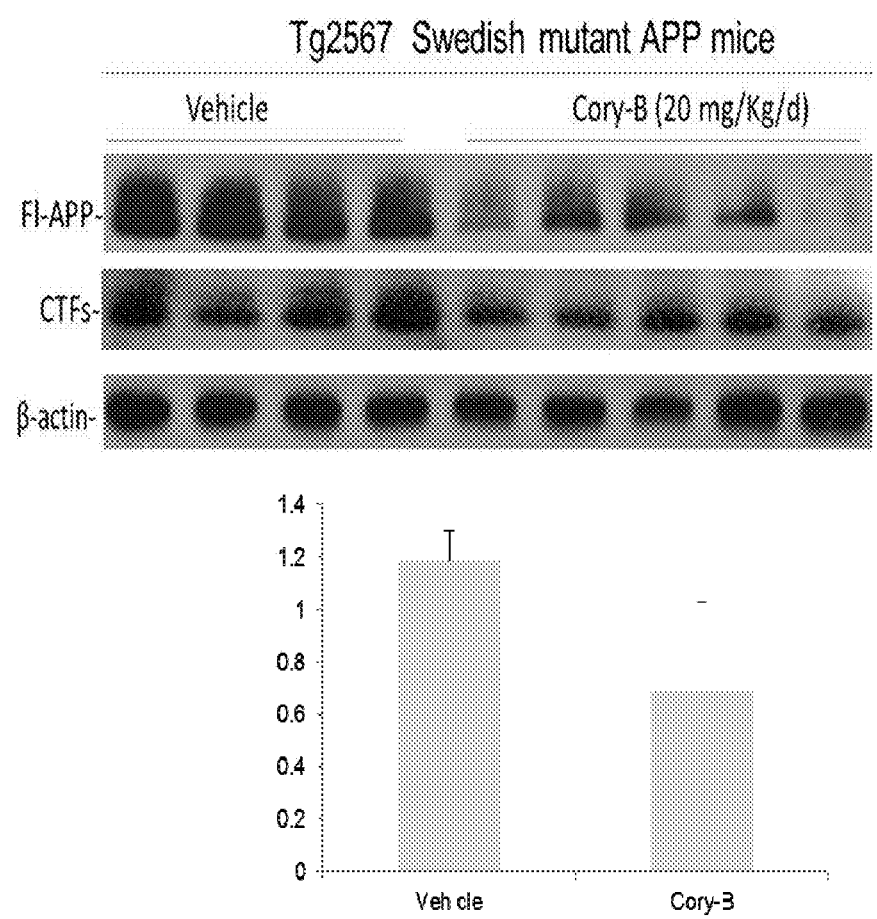

N2a Swedish APP cells are incubated with different concentration of Cory and Cory B in the presence or absence of CQ and 3MA. Cory and CoryB dose-dependently reduce both full length and CTF APP via autophagy (FIG. 9A, 9B). Tg2567 APP mice, 3 months old JNPL P301 Tau mice and WT mice intraperitoneally are administrated with 20 mg/kg/d CoryB. Three months of Cory-B treatment significantly decrease total tau and Fl-APP/CTF in JNPL tau mice and Tg2567, respectively (FIG. 9C, 9D). There is a remarkable increase in LC3-II levels and in the tau clearance by Cory-B-treatment in Tau mice (FIG. 9C).

Example IX

Figure 10A:
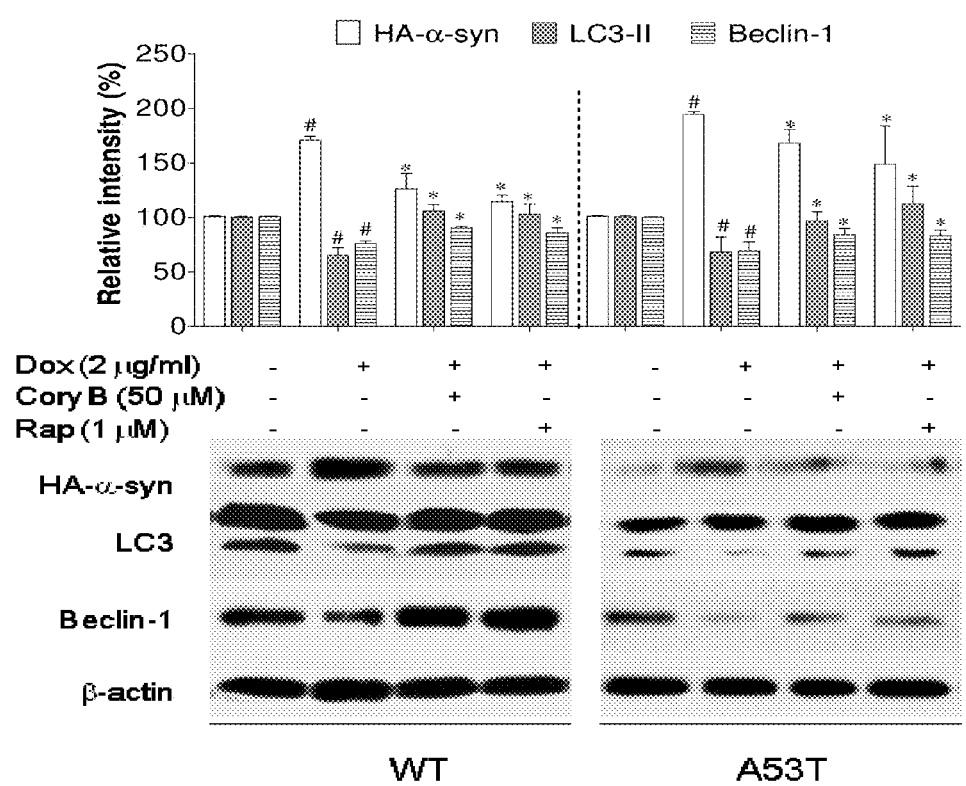
FIG. 10: Corynoxine B restored the deficient cytosolic translocation of HMGB1 and autophagy caused by α-syn overexpression. Western blot analysis of induced HA-α-syn, endogenous LC3-II and Beclin-1 in alpha-synuclein Inducible PC12 cells (FIG. 10A). Western blot analysis of expression level of HMGB1 in the cytosolic and nuclear fractions (FIG. 10B).
Figure 10B:
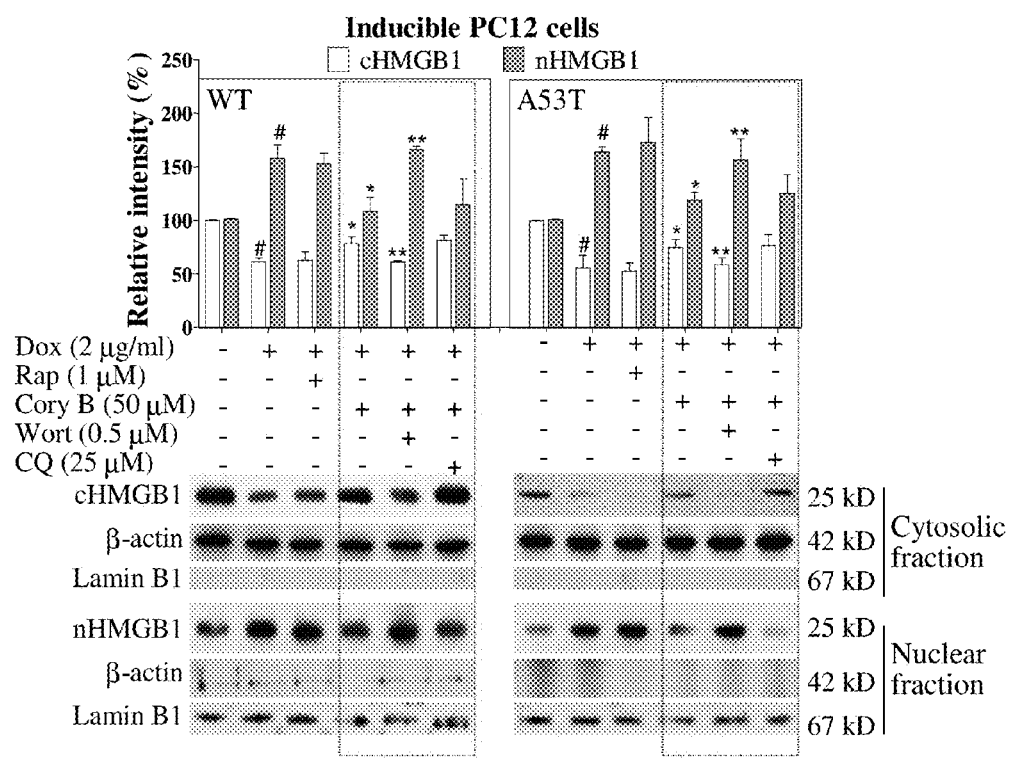

Corynoxine B Restores the Deficient Cytosolic Translocation of HMGB1 and Autophagy Caused by α-Syn Overexpression Inducible PC12 cells are treated with 2 mg/ml Dox for 24 h in the presence of Corynoxine B (Cory B), rapamycin (Rap), wortmannin (Wort) or chloroquine (CQ). The expressions of induced HA-α-syn, endogenous LC3-II and Beclin-1 are determined by Western blotting (FIG. 10A). The expression of HMGB1 in the cytosolic and nuclear fractions are determined by Western blotting (FIG. 10B). b-actin and Lamin B1 are used as relative loading controls. Data are presented as the mean±SD from three independent experiments. #$p<0.05$ vs. un-induced control; *$p<0.05$ vs. Dox treatment; **$p<0.05$ vs. Dox+Cory B treatment.

Based on the working examples, it is demonstrated that pro-autophagy activity of Cory B is highly responsive in neuronal cells. It induces substantial autophagy in a wide range of neuronal cell lines (N2a, SH-SY5Y and PC12) as well as in primary neuron cultures as illustrated by the increase of LC3-II/actin ratio and GFP-LC3 puncta formation. While it is well-known that α-syn can be degraded either by proteasomes, macroautophay and chaperone-mediated autophagy (CMA), only the two autophagy pathways are capable of degrading α-syn. More specifically, it has been reported that mutant α-syn inhibits CMA and only macroautophagy can degrade mutant α-syn. The working examples show that Cory B specifically enhances macroautophagy and significantly degrades WT, mutant alpha-synuclein monomers, alpha-synuclein oligomers as well as alpha-synuclein/synphilin-1 aggresomes in different human DA cells which is not shown in previous chemical autophagy inducers like rapamycin, trehalose and 17-AAG. The mTOR independent autophagy-inducing effect of Cory B demonstrated also means that treatment of diseases that benefit from autophagy with the present invention eliminates any side-effects or complications related to the mTOR pathway.

*Drosophila* larvae have proven to be useful in exploring the molecular mechanisms as well as the physiological functions of autophagy in vivo. Therefore, the demonstration of the present invention that Cory B is capable of inducing autophagy in *drosophila* L3 larvae fat body illustrates in vivo autophagy induction ability thereof.

Synthesis of Synthetic Analogues of Cory B

In one embodiment of the present invention, eleven synthetic analogues of the compound Cory B have been synthesized via the five Schemes.

Synthesis of Cory B Analogues

One embodiment of the present invention focuses on C-22 ester interchange and N-1 substituted group and synthesized eleven new analogues of Cory B. The synthetic schemes are listed as follow:

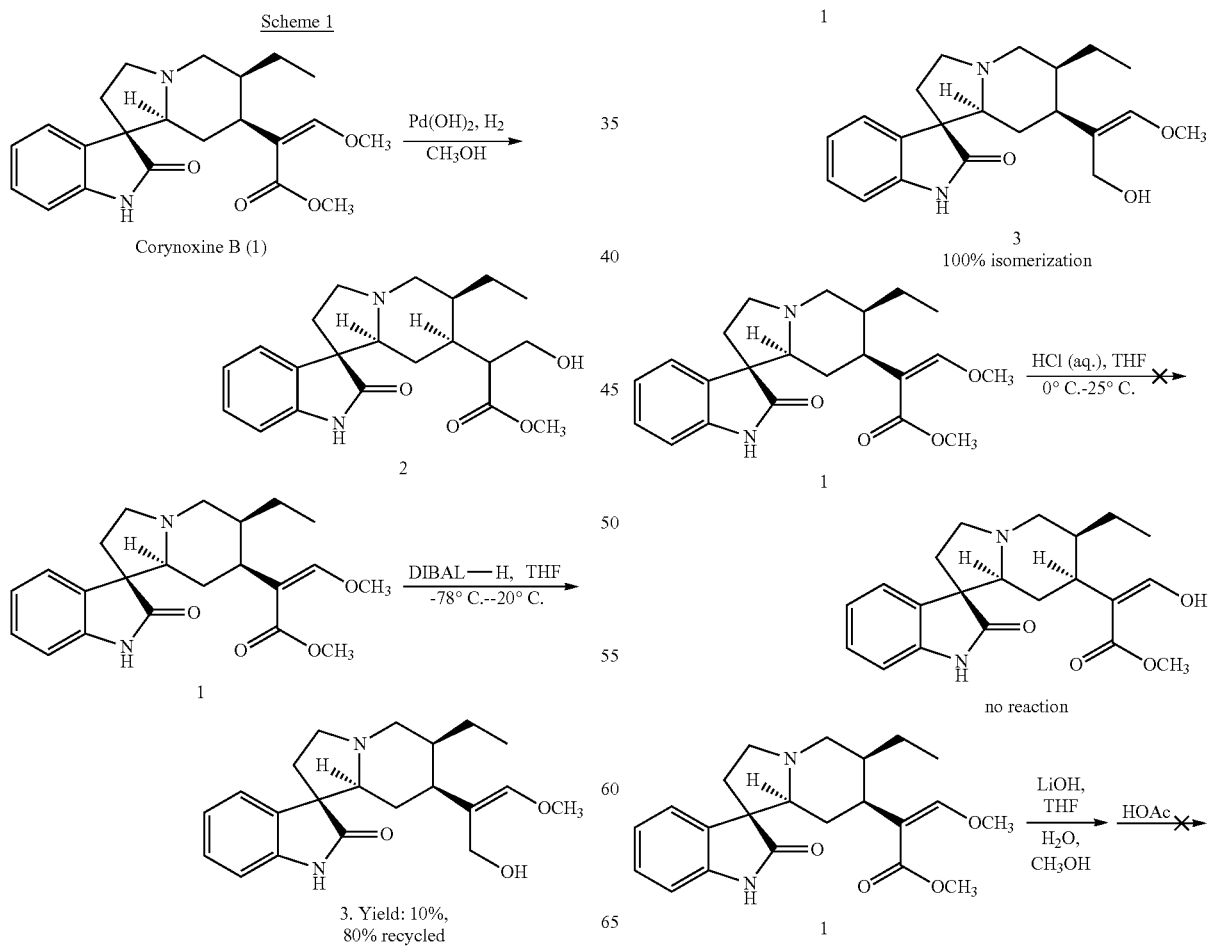

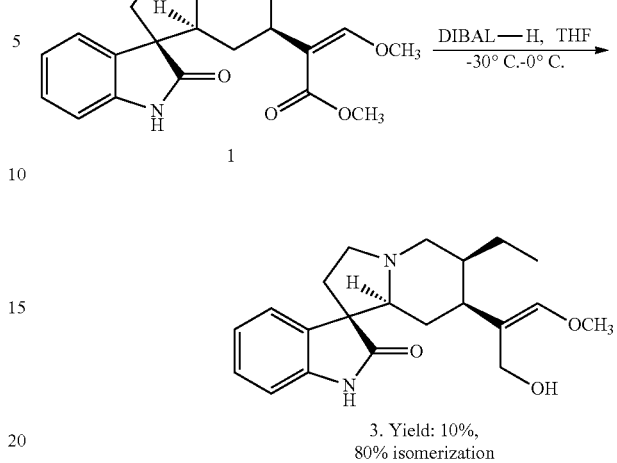

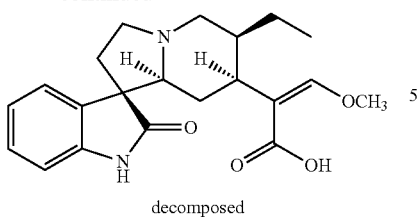

decomposed

In the Scheme 1, according to an embodiment of the present invention, firstly the diastereomer compound 2 is obtained through the double bonds in Corynoxine B (1) reduction with H$_2$, secondly compound 3 is obtained through the ester group in Corynoxine B (1) reduction with DIBAL-H. The yield of above reaction is less than 10% and most starting material can be recycled. The yield is still low even if the reaction temperature rises to 0 centigrade because Corynoxine B (1) becomes Corynoxine when the temperature rises to 0 centigrade. The corresponding product cannot be obtained when Corynoxine B reacts with BH$_3$ at 0-25 centigrade as all the starting material becomes Corynoxine. In acidic condition, the Corynoxine B is too stable to hydrolyse the ether bond. In basic condition, the Corynoxine B is decomposed thoroughly when it is exposed in the solution of Lithium hydroxide.

Scheme 2

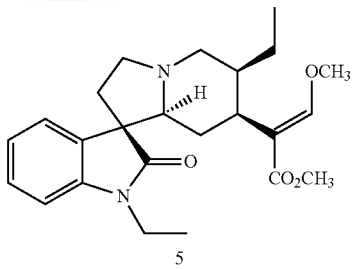

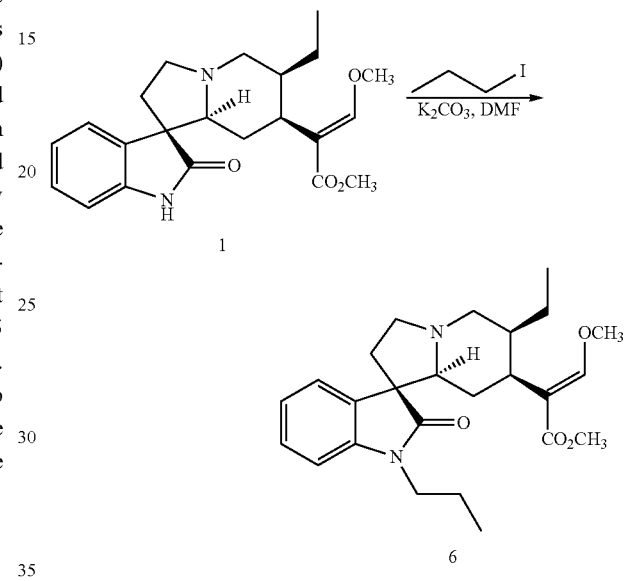

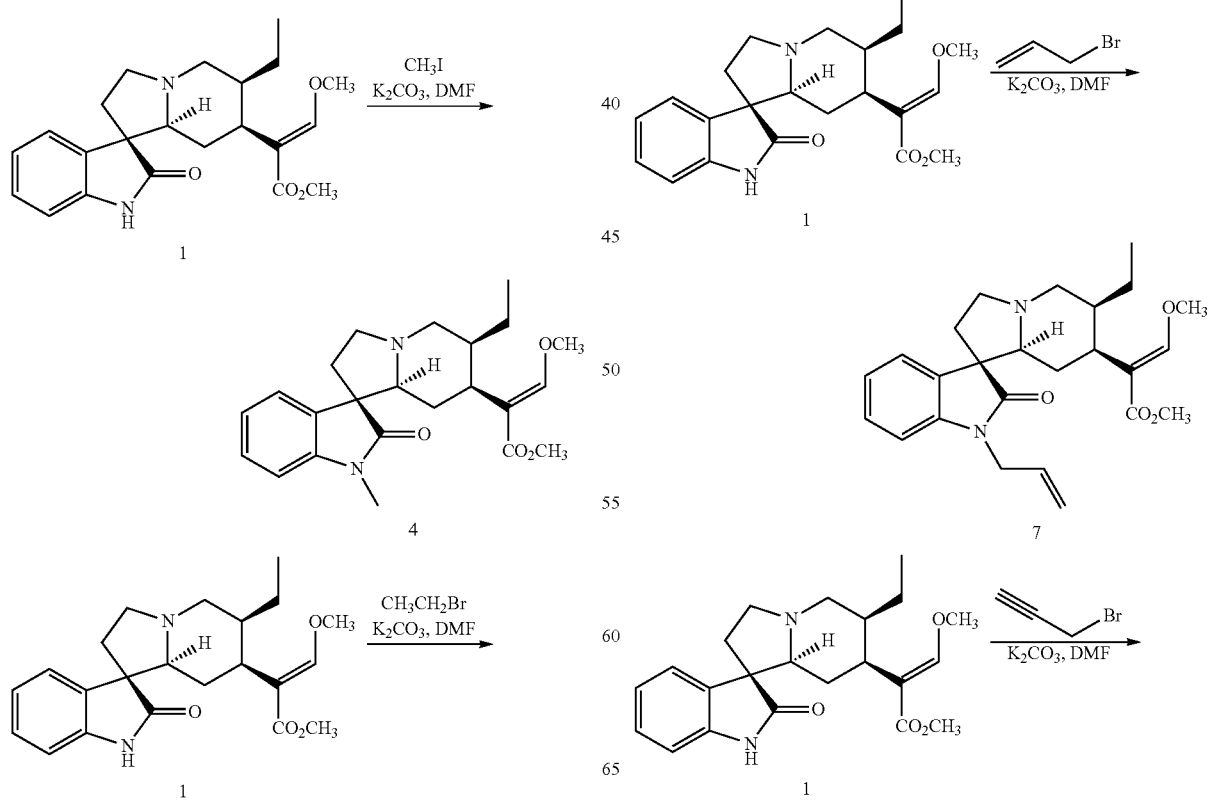

-continued

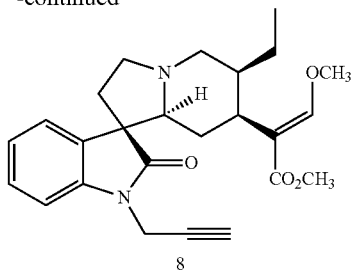

8

In the Scheme 2, compounds 4-8 are obtained through Corynoxine B reacting with methyl iodide, bromoethane, iodine propane, allyl bromide and propargyl bromide in the solution of DMF.

Scheme 3

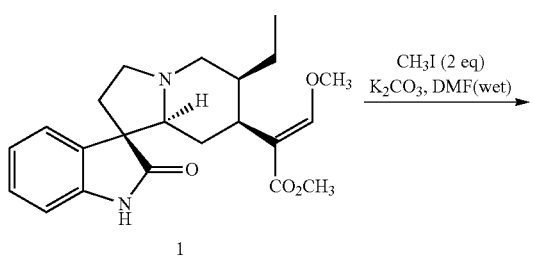

1

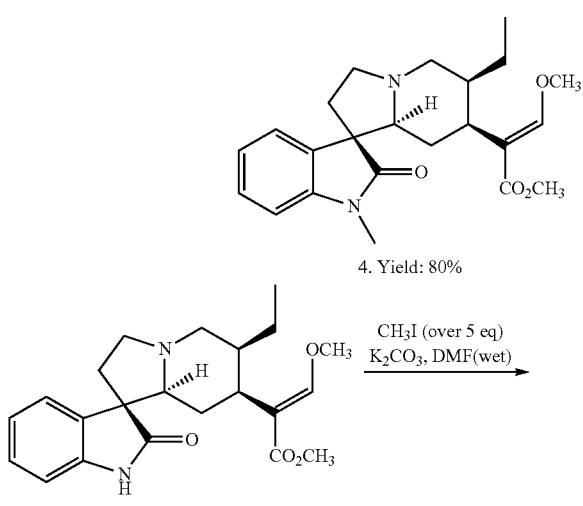

In the Scheme 3, the yield of compound 4 could be improved to 80% when Corynoxine B reacts with methyl iodide and potassium carbonate in wet DMF. Compound 9 can be obtained through Corynoxine B reacts with five equivalent methyl iodide and potassium carbonate in wet DMF.

Scheme 4

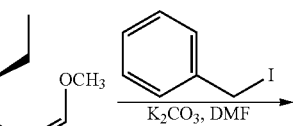

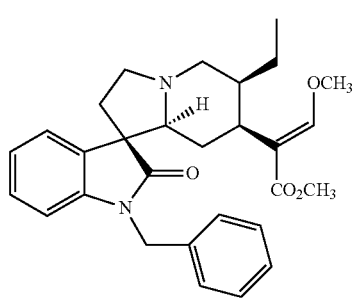

10. Yield: 15%
HRMS, $^1$H NMR

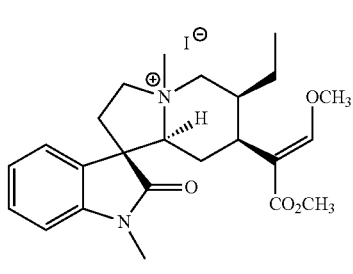

11. Yield: 10%
HRMS, unstable

In the Scheme 4, the yield of compound 10 is less than 15% when Corynoxine B reacts with benzyl iodine and potassium carbonate in wet DMF. The yield of compound 11 is less than 10% when Corynoxine B reacts with (E)-1-bromo-2, 7-dimethylocta-2, 6-diene and potassium carbonate in wet DMF. And the compound 11 is sensitive to silica gel in separation.

Scheme 5

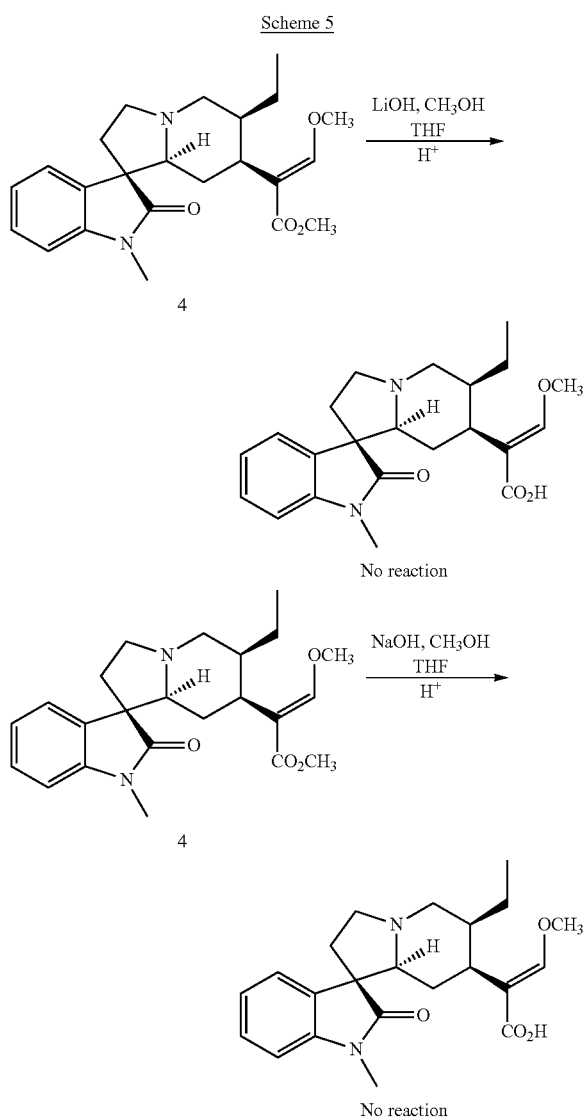

No reaction

No reaction

In the Scheme 5, some analogs of compound 4 are synthesized based on biological activity and structure character. Compound 4 could not be hydrolyzed in the solution of lithium hydroxide. Even if in the solution of sodium hydroxide, compound 4 still could not be hydrolyzed to get the carboxyl compound.

In an embodiment of the present invention, the synthetic compound identified as compound 6 and compound 7 in Scheme 2 is labeled as CB6 and CB8 and compound 1 is Corynoxine B.

Synthesis of CB6 and CB8

CB6 and CB8 are obtained through Corynoxine B reacts with iodine propane and allyl bromide respectively with potassium carbonate in the solution of DMF. This is presented in Scheme 2. From the process of Scheme 2, the synthesized compounds of CB6 and CB8 are presented as light yellow oil with the synthesis yield of approximately 45% for CB6 and approximately 50% for CB8. Both with the reaction temperature of about 25° C.

Examine the Pro-Autophagic Activities of the Synthesized Cory B Analogues

CB6 induce autophagy in N2a cells

Figure 11:
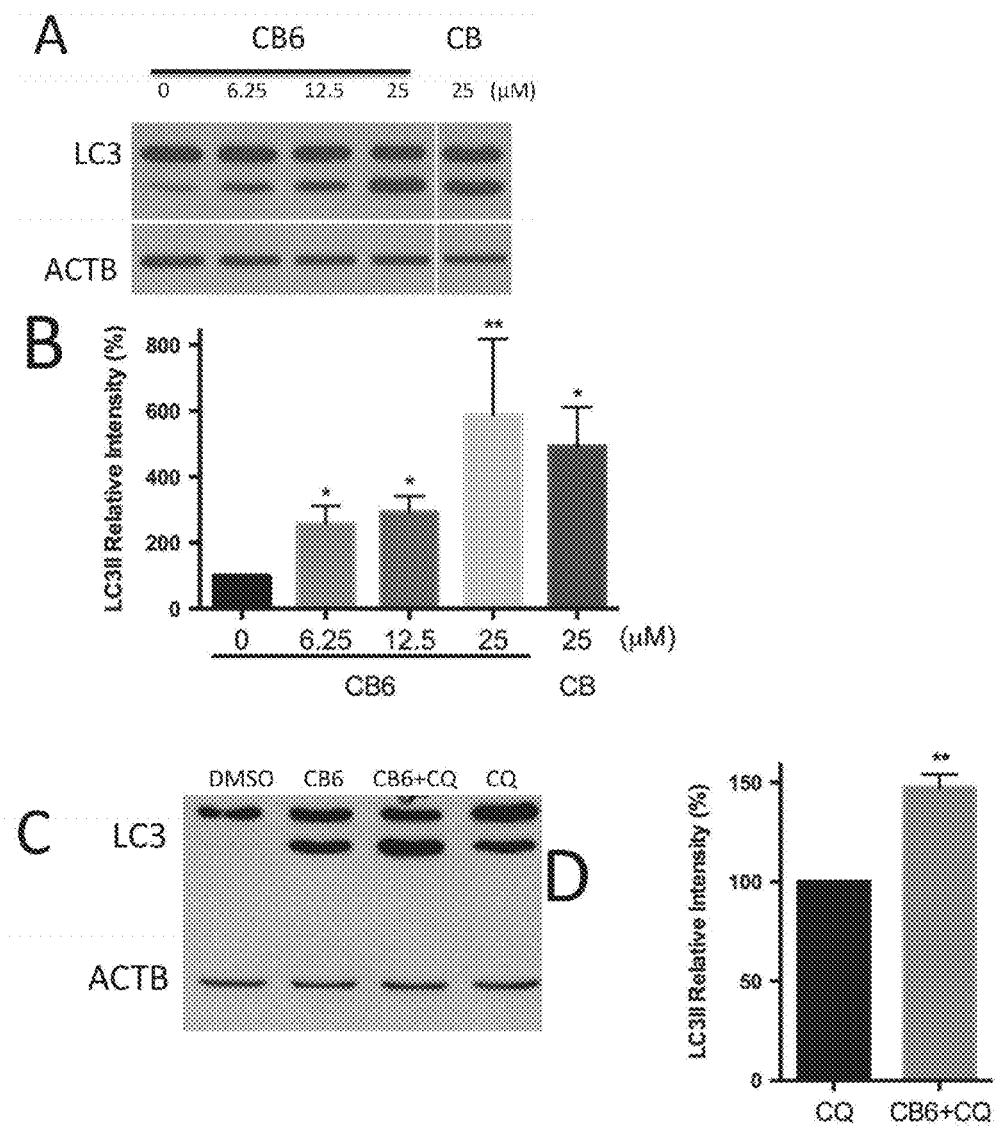
FIG. 11: CB6 induces autophagy in N2a cells. Western blot analysis of the expression level of autophagy marker, LC3-II, in N2a cells treated with different concentrations of CB6 for 12 hrs, in comparison with CB (A), and the LC3II relative intensity of each treatment (B); and N2a cells induced by 25 μM and/or 30 μM lysosome inhibitor chloroquine (CQ) for 12 hrs (C), and the LC3II relative intensity of CQ and CQ+CB6 (D).

In order to examine the pro-autophagic activities of the synthesized Cory B analogues, neuroblastoma 2a, a neuronal cell line, are treated with various concentrations of the analogues for 12 hrs. The cells are then harvested and lysed with RIPA buffer (150 mM NaCl, 50 mM Tris-HCl pH 7.4, 0.35% sodium deoxycholate, 1 mM EDTA, 1% NP40, 1 mM PMSF, 5 µg/ml aprotinin, 5 µg/ml leupeptin). The sample are lysed on ice with occasional vortex for 30 min, and then centrifuged at 14,000 rpm for 15 min at 4° C. The supernatant are collected and denatured at 95° C. in sample buffer for 5 min. The denatured samples are then separated on 15% SDS-PAGE gels and transferred to PVDF membrane. Membranes are then blocked with 5% non-fat milk and probed with appropriate primary and secondary antibodies. The protein signals of LC3II, marker protein of autophagy, are finally visualized with ECL kit and the protein bands density are quantified by ImageJ program. As shown in FIG. 11, CB6 is discovered as a novel autophagy inducer.

CB8 induce autophagy in N2a cells

Figure 12:
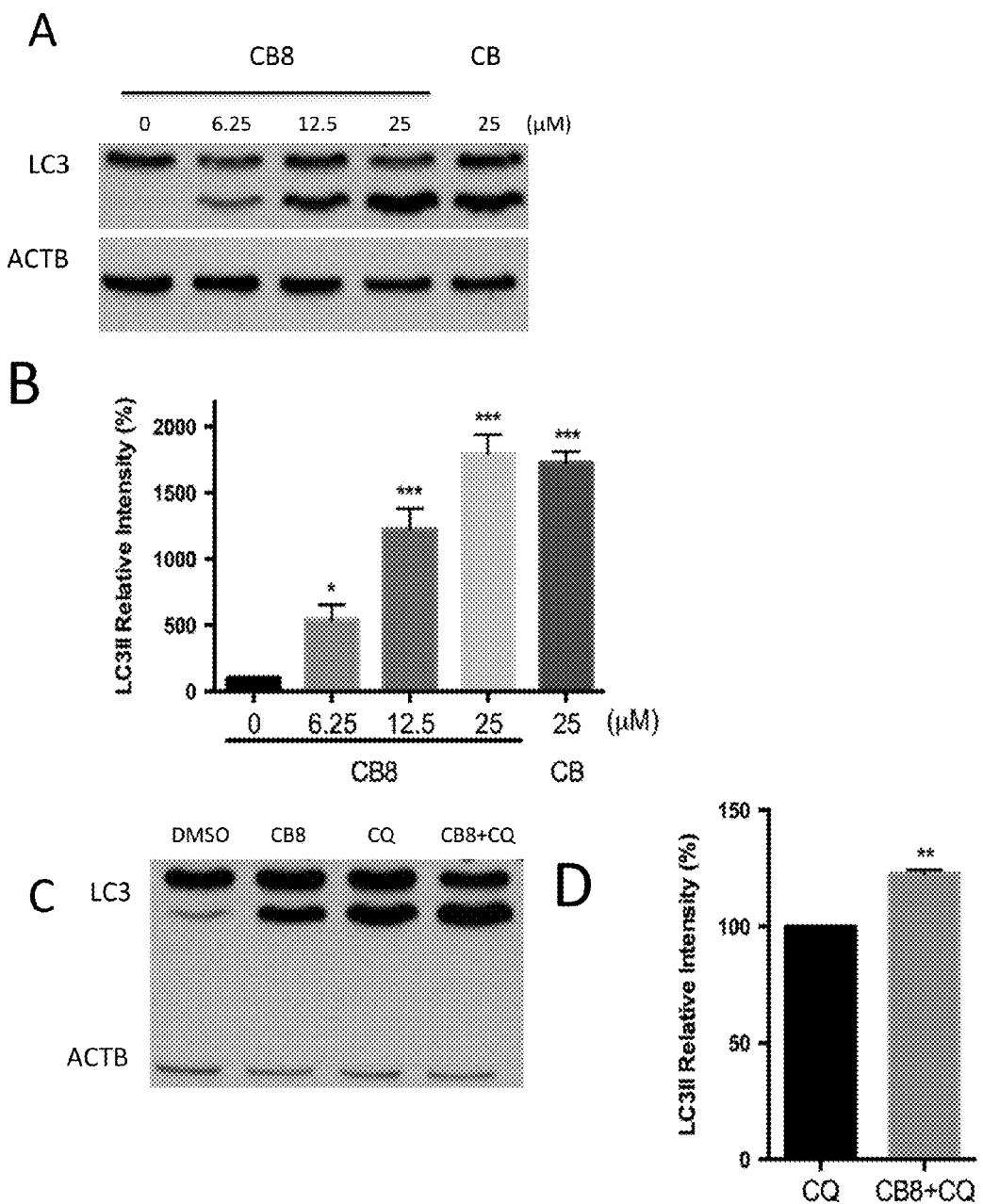
FIG. 12: CB8 induce autophagy in N2a cells. Western blot analysis of the expression level of autophagy marker, LC3-II, in N2a cells treated with different concentrations of CB8 for 12 hrs, in comparison with CB (A), and the LC3II relative intensity of each treatment (B); and N2a cells induced by 25 μM and/or 30 μM lysosome inhibitor chloroquine (CQ) for 12 hrs (C), and the LC3II relative intensity of CQ and CQ+CB8 (D).

As shown in FIG. 12, similar to CB6, CB8 is also proved to be a novel autophagy inducer. The experiment set up is the same as the one used in the experiment for CB6 inducing autophagy in N2a cells.

CB6 and CB8 induce autophagy in N2a-GFP-LC3 cells

Figure 13:
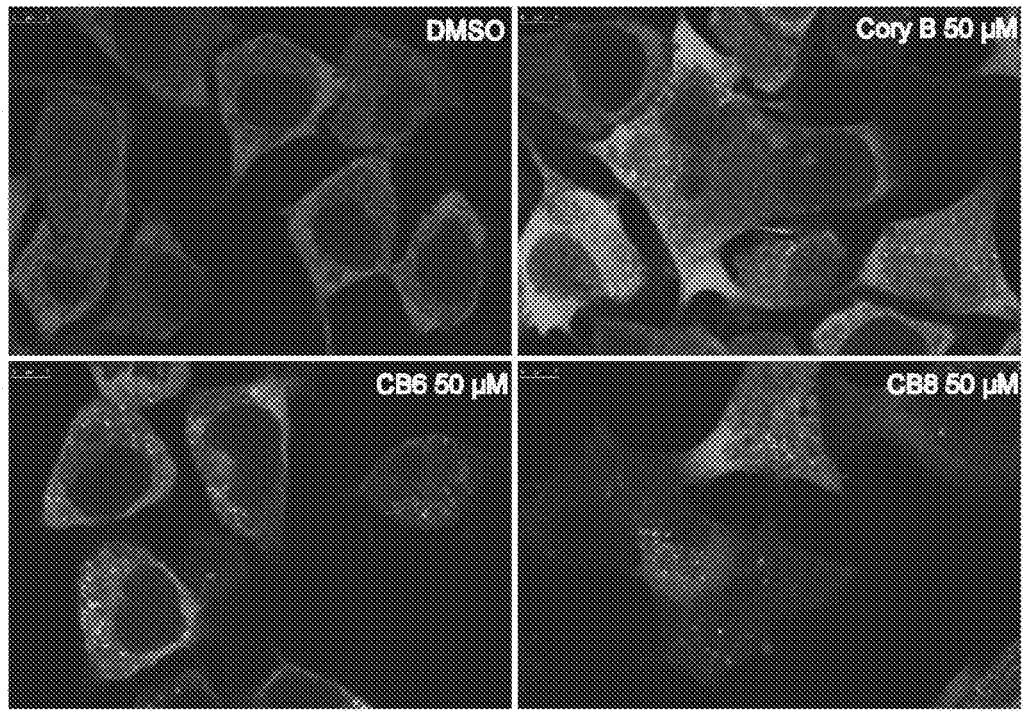
FIG. 13: Florescene images of N2a-GFP-LC3 cells treated with CB6 and CB8. CB6 and CB8 induce autophagy in N2a-GFP-LC3 cells. N2a cells constantly expressing GFP-LC3 were treated with DMSO, 50 μM of Cory B, CB6 and CB8 for 12 hours respectively. Similar to Cory B, CB6 and CB8 were able to up-regulate the GFP-LC3 puncta (green dots in the cells) formation.

In order to observe the pro-autophagic activity of CB6 and CB8 intuitively, N2a cells constantly expressing GFP-LC3 are treated with 50 µM Cory B, CB6 and CB8 for 12 hours respectively. The cells are than fixed with 4% paraformaldehyde (Sigma, 158127) for 10 minutes, and then mounted with VECTASHIELD hardset anti-fade mounting medium. The mounted samples are then subjected to confocal microscopy analysis. As shown in FIG. 13, CB6 and CB8 are confirmed to be autophagy inducers.

CB6 and CB8 induce autophagy in primary neurons

Figure 14:
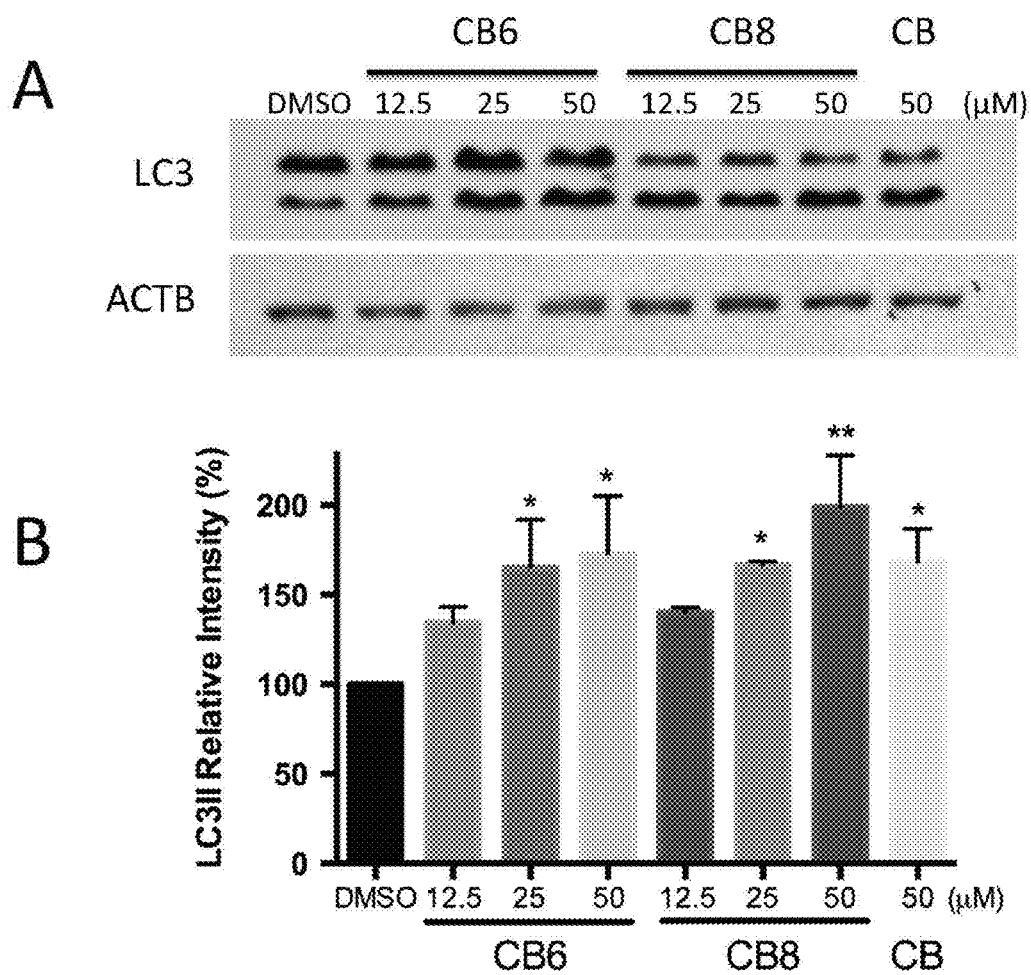
FIG. 14: CB6 and CB8 induce autophagy in primary neurons. Western blot analysis of the expression level of autophagy marker, LC3-II, primary cultured E17 embryonic rat cortical neurons induced by different concentrations of CB6 and CB8 for 12 hrs, in comparison with CB (A), and the LC3II relative intensity of each treatment (B).

To further confirm the pro-autophagic effect of CB6 and CB8 on primary neurons, rat primary cortical neurons isolated from E17 rats are used in the study. The primary neurons are treated with different concentrations of CB6 and CB8 respectively for 24 hours, and autophagic markers LC3 is detected by immunoblot analysis. As shown in FIG. 14, CB6 and CB8 induced autophagy in primary cultured rat cortical neurons.

CB6 and CB8 induce autophagy in vivo

Figure 15:
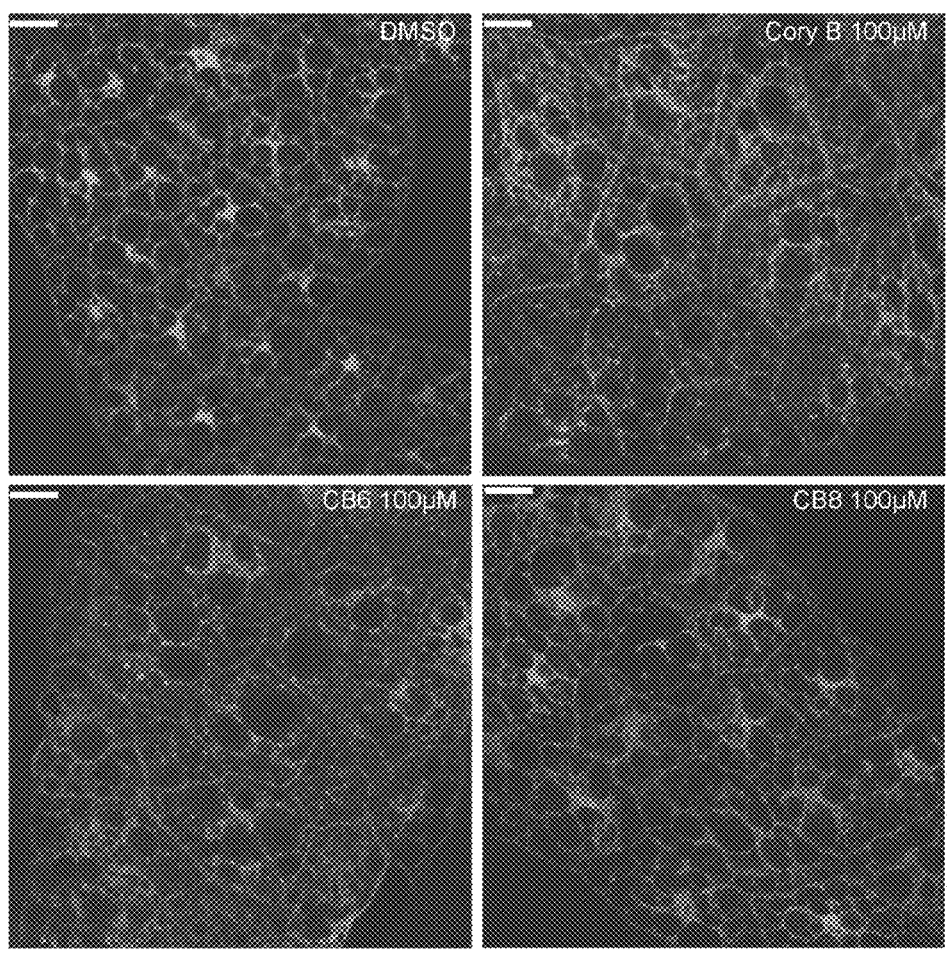
FIG. 15: CB6 and CB8 induce autophagy in vivo. *Drosophila* carrying Atg8a-EGFP transgene were crossed with Cg-GAL4 flies. After 90 hours of oviposition. The L3 larvae were treated with 100 μM of Cory B, CB6 and CB8 for 6 hrs respectively. The fat bodies were harvested and analyzed under confocal fluorescence microscope. The typical image of each treatment was shown. Similar to Cory B, both of CB6 and CB8 induced Atg8a-EGFP puncta (green dots) formation in *Drosophila* fat body.

To further test whether CB6 and CB8 could induce autophagy in vivo, Drosolphila expressing Atg8a-GFP (Atg8a, Drosophila homologue of LC3) are obtained by crossing Cg-GAL4, a GAL4 line drives transgene expression in fat body, with UAS-Atg8a-EGFP. Crossed flies are allowed to lay eggs for 1 hour, 90 hours later, the L3 larvae are collected and treated with 100 µM of Cory B, CB6 and CB8 for 6 hours respectively. After treatment, the fat body lobes of the larvae are harvested with fine forceps and fixed with 4% PFA in PBS at room temperature for 15 minutes. Fat body lobes are then washed with PBS three times and subsequently mounted with VECTASHIELD hardset antifade mounting medium. The slides are then subjected to confocal microscopy analysis. As shown in FIG. 15, CB6 and CB8 are able to induce autophagy in Drosophila fat body.

Examine the α-synuclein clearance activity of CB6 and CB8

Figure 16:
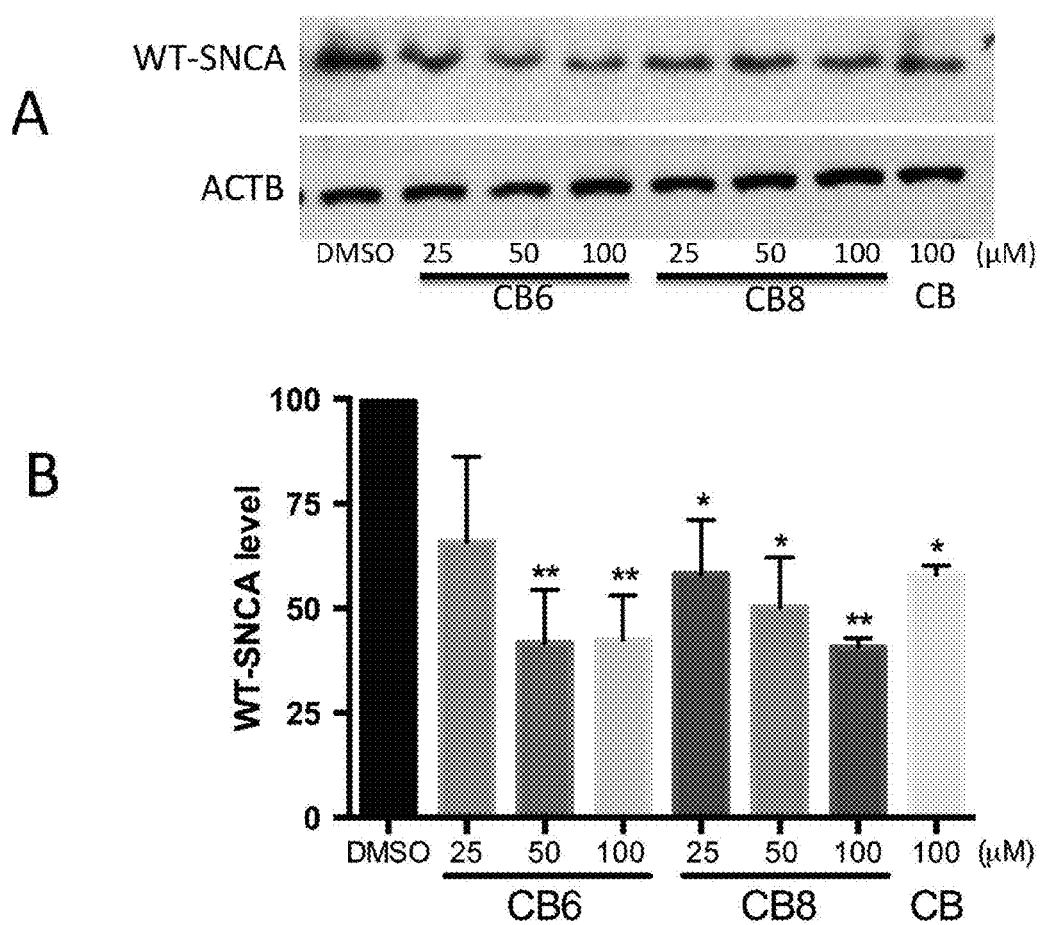
FIG. 16: CB6 and CB8 promote α-synuclein clearance in *Drosophila* PD model. Typical blot of α-synuclein in the brains of transgenic *Drosophila*, which were treated with different dosages of CB6, CB8 and CB for 30 days (A), and the α-synuclein level of each treatment (B).

The pathological hallmark of PD is the abnormal accumulation of α-synuclein (SNCA). Promoting clearance of α-synuclein via enhancing autophagy is a potential therapeutic strategy of PD treatment. In the previous embodiment of the present invention CB6 and CB8 are proved to be autophagy inducers both in vitro and in vivo. To test whether CB6 and CB8 could promote the clearance of α-synuclein in vivo, elav-GAL4, which drive transgene expression in all neurons and UAS-SNCA$^{wt}$ that carrying the wild type human SNCA gene are crossed. The progeny are treated with different dosages of CB6 and CB8 for thirty days. At the end of the treatment, twenty fly heads are homogenized in lysis buffer (50 mM Tris, 1% NP-40, 0.35% sodium deoxycholate, 150 mM NaCl, 1 mM EDTA, 1 mM EGTA, 1 mM PMSF, pH7.4) and lysed on ice for 20 min. The supernatants are collected after centrifugation (14,000 rpm, 10 min, 4° C.) and denatured with 5× Laemmli sample buffer and then separated on 12% SDS-PAGE gels. The protein on the gels are then transferred to PVDF membranes (GE Healthcare, RPN303F) and processed for immunoblotting. Membranes are blocked with 5% nonfat milk and probed with primary and secondary antibodies. The bands are developed with an ECL kit (Pierce, 32106). The density of the bands is quantified by densitometry (ImageJ, NIH). The results are obtained from three independent experiments and shown in FIG. 16.

Pharmacokinetic study of CB6 and CB8

Male Sprague-Dawley (SD) rats (weighting ~200 g) used in the experiment are provided by Laboratory Animal Services Center of The Chinese University of Hong Kong (Hong Kong SAR, People's Republic of China). Cory B (n=3), CB6 (n=6) and CB8 (n=6). For the jugular vein cannulation surgery, the rats are anesthetized (intramuscular injection of a mixture of 80 mg/kg ketamine and 8 mg/kg xylazine) followed by inserting a polyethylene tube (0.5 mm ID, 1 mm OD, Portex Ltd., England) into the right jugular vein. The cannulated rats are allowed to recover overnight while fasting with free access to water. For intravenous (IV) administrations, Cory B, CB6 or CB8 (200 μg/mL, dissolved in saline containing 9.2% PEG400+0.5% DMSO, w/w) is given through the jugular vein catheter at 1 mg/kg. For intranasal (IN) administration, 10 μL of Cory B, CB6 or CB8 (10 mg/mL, dissolved with 40% PEG400, 10% DMSO in H2O, w/w) is given to each nostril of rats. At pre-determined time points post-dosing (5, 10, 20, 30, 60, 120, 240 and 360 min for IV and IN administration groups), approximately 200 μL blood is collected into a heparinized centrifuge tube containing 5 μM EDTA followed by centrifugation at 3000 rpm for 5 min to obtain the plasma. To 100 μL rat plasma sample, an aliquot of 100 μL internal standard (IS) and 100 μL of acetonitrile are added. The mixture is mixed for 1 min by vortex and then centrifuged for 10 min at 13,200 rpm. 200 μL of supernatant is transferred into centrifuge tubes and mixed with 200 μL of H$_2$O containing 4% formic acid (FA). After another round of vortex and centrifugation, 10 μL of the supernatant is subjected to LC/MS/MS for quantification of Cory B, CB6 or CB8 with an established LC/MS/MS method. Pharmacokinetic parameters from non-compartmental analysis (NCA) are calculated using WinNonLin. The pharmacokinetic parameters and profiles of each analytes are shown as below.

TABLE 1

Pharmacokinetics parameters of Cory B, CB6 and CB8 (Intravenous)

| Intravenous | $t_{1/2}$ (min) | $T_{max}$ (min) | $C_{max}$ (ng/mL) | AUC (min * ng/mL) | MRT (min) |
|---|---|---|---|---|---|
| Cory B | 128 ± 22 | — | 66 ± 8 | 3814 ± 206 | 138 ± 31 |
| CB6 | 120 ± 15 | — | 520 ± 177 | 14871 ± 2646 | 95 ± 15 |
| CB8 | 112 ± 26 | — | 143 ± 42 | 6108 ± 1449 | 99 ± 9 |

$t_{1/2}$: plasma half-life;
$T_{max}$: time to reach $C_{max}$;
$C_{max}$: maximum plasma concentration;
AUC: area under the curve;
MRT: mean residence time.

TABLE 2

Pharmacokinetics parameters of Cory B, CB6 and CB8 (Intranasal)

| Intranasal | $t_{1/2}$ (min) | $T_{max}$ (min) | $C_{max}$ (ng/mL) | AUC (min * ng/mL) | MRT (min) |
|---|---|---|---|---|---|
| Cory B | 116 ± 14 | 5 ± 0 | 145 ± 62 | 5558 ± 1396 | 133 ± 26 |
| CB6 | 116 ± 8 | 5 ± 0 | 244 ± 33 | 12023 ± 1421 | 110 ± 33 |
| CB8 | 99 ± 13 | 5 ± 0 | 129 ± 61 | 7448 ± 3452 | 117 ± 32 |

Figure 17A:
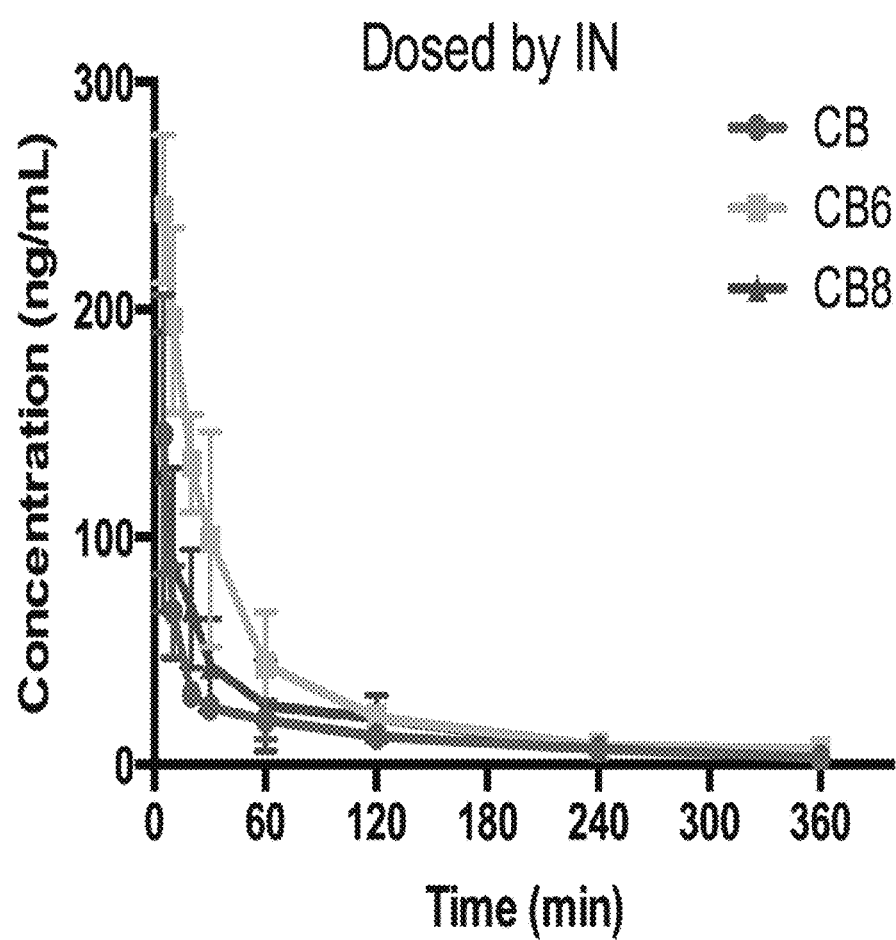
FIG. 17A: The plasma concentration versus time profiles of Cory B, CB6 and CB8 followed similar patterns after IN administration of 1 mg/kg of each analytes in rats.
Figure 17B:
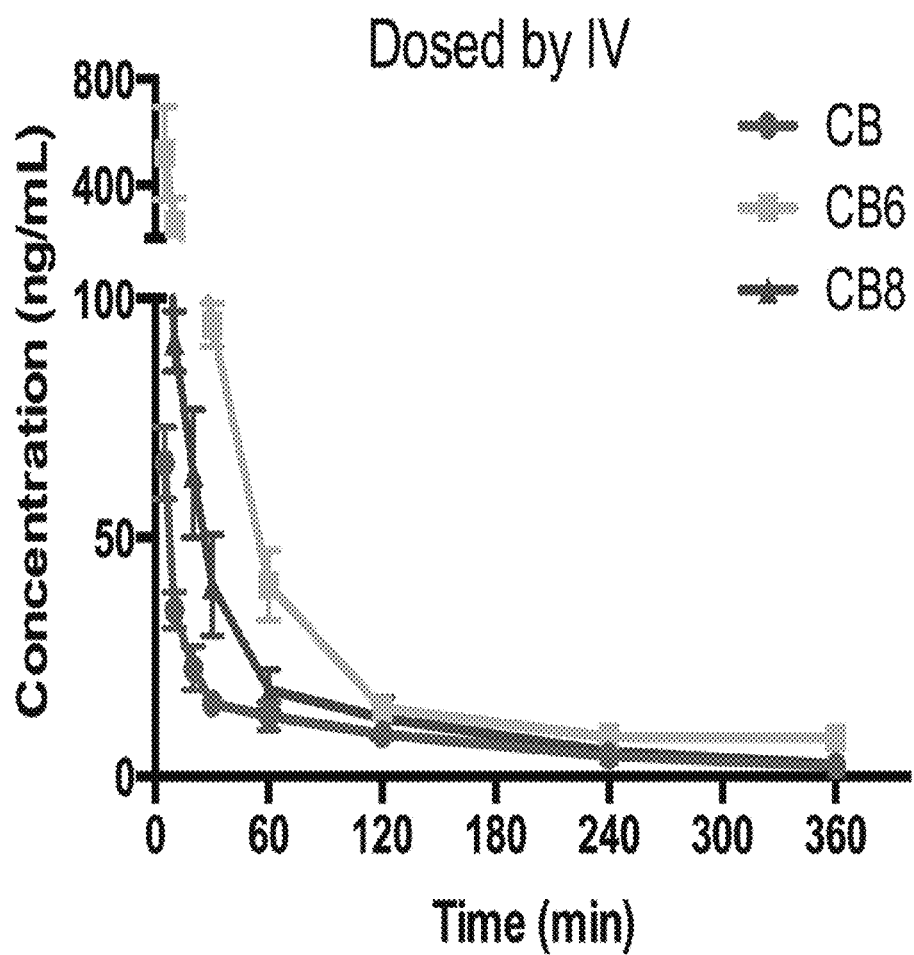
FIG. 17B: The plasma concentration versus time profiles of Cory B, CB6 and CB8 followed similar patterns after IV administration of 1 mg/kg of each analytes in rats

As shown in FIG. 17, the plasma concentration versus time profiles of Cory B, CB6 and CB8 follow similar patterns after IV and IN administration of 1 mg/kg of each analytes in rats. Pharmacokinetics parameters determined based on NCA in Table 1 and Table 2 indicated that all of these compounds undergo fast elimination in vivo, with no significant difference observed among the studied two routes. However, CB6 and CB8 have greater $C_{max}$ and Area Under Curve (AUC) in comparison Cory B. This is an indication that the structure modifications in CB6 and CB8 significantly increase the exposure of the synthetic analogues and thus increased their pharmacokinetic characteristics. The AUC (from zero to infinity) represents the total drug exposure over time. Assuming linear pharmacodynamics with elimination rate constant K, one can show that AUC is proportional to the total amount of drug absorbed by the body (i.e. the total amount of drug that reaches the blood circulation). The proportionality constant is 1/K. $C_{max}$ is a term used in pharmacokinetics refers to the maximum (or peak) serum concentration that a drug achieves in a specified compartment or test area of the body after the drug has been administrated and prior to the administration of a second dose. Thus, in one embodiment of the present invention, the synthesized Cory B analogues, CB6 and CB8, exhibit a higher total absorption amount in the body and a higher concentration of these Cory B analogues in the body when compared to the natural Cory B.

Characterisation of analogue CB6

Physical characteristic: Light yellow oil, Yield: 45%;
$^1$H-NMR (400 MHz, CDCl$_3$) δ: 7.30 (s, 1H), 7.15-7.25 (m, 2H), 6.95-7.06 (m, 1H), 6.75-6.80 (m, 1H), 3.85-3.95 (m, 1H), 3.65 (s, 3H), 3.62 (s, 3H), 3.35-3.45 (m, 1H), 3.20-3.30 (m, 2H), 2.55-2.65 (m, 1H), 2.32-2.45 (m, 2H), 2.10-2.30 (m, 2H), 1.92-2.08 (m, 3H), 1.75-1.85 (m, 1H), 1.63-1.70 (m, 3H), 1.43-1.50 (m, 1H), 0.95 (t, J=7.2 Hz, 3H), 0.87 (t, J=7.2 Hz, 3H).

$^{13}$C-NMR (100 MHz, CDCl$_3$): 178.9, 169.2, 160.4, 143.4, 133.5, 127.6, 122.9, 121.9, 111.3, 107.5, 61.5, 55.8, 55.0, 54.8, 51.3, 41.4, 40.3, 34.1, 29.7, 25.0, 24.8, 20.9, 19.1, 13.2, 11.4.

Characterisation of analogue CB8

Physical characteristic: Light yellow oil, Yield: 50%;

$^1$H-NMR (400 MHz, CDCl$_3$) δ: 7.30 (s, 1H), 7.15-7.23 (m, 2H), 7.03 (t, J=7.6 Hz, 1H), 6.72 (d, J=7.6 Hz, 1H), 5.75-5.85 (m, 1H), 5.10-5.20 (m, 2H), 4.60-4.70 (m, 1H), 4.00 (dd, J=12.0, 4.4 Hz, 1H), 3.67 (s, 3H), 3.61 (s, 3H), 3.20-3.35 (m, 2H), 2.55-2.65 (m, 1H), 2.35-2.45 (m, 2H), 2.15-2.26 (m, 2H), 1.95-2.08 (m, 2H), 1.70-1.82 (m, 1H), 1.43-1.50 (m, 1H), 1.10-1.20 (m, 1H), 0.95-1.05 (m, 1H), 0.85 (t, J=7.6 Hz, 3H).

$^{13}$C-NMR (100 MHz, CDCl$_3$): 178.7, 169.1, 160.4, 143.0, 133.2, 132.0, 127.6, 122.8, 122.3, 116.6, 111.3, 108.3, 61.5, 55.9, 55.0, 54.8, 51.3, 42.2, 40.2, 34.0, 29.7, 25.1, 19.1, 13.2.

Experimentation Data for Cb6 and Cb8

Reagents and antibodies

Chloroquine (C6628), doxycycline (D9891), paraformaldehyde (158127) were purchased from Sigma-Aldrich. Rapamycin (R5000) was purchased from LC Laboratories. ACTB/β-actin (sc-47778) was purchased from Santa Cruz Biotechnology. Anti-LC3 (2775) and mouse anti-rabbit IgG were purchased from Cell Signaling Technology. α-Syn (SNCA) antibody (610786) was purchased from BD Transduction Laboratories. DMEM (11965-126), DMEM/F12 (12634-010), Neural basal medium (21103-049) horse serum (16050-122), fetal bovine serum (FBS) (16000-044), G418 (10131-035), goat anti-mouse-HRP (626520), goat anti-rabbit-HRP (G21234) were purchased from Invitrogen.

Cell culture

N2a cells and N2a cells stable expressing GFP-LC3 were cultured in DMEM, supplemented with 10% FBS at 37° C., 5% CO$_2$.

Fluorescence analysis of LC3 puncta

After designated treatments, N2a cells constantly expressing GFP-LC3 were fixed with 4% paraformaldehyde (Sigma, 158127) for 10 min, and then mounted with VECTASHIELD hardset antifade mounting medium. The mounted samples were then subjected to confocal microscopy analysis.

Protein samples preparation and immunoblot analysis

After designated treatments, the cells were lysed with RIPA buffer (150 mM NaCl, 50 mM Tris-HCl pH 7.4, 0.35% sodium deoxycholate, 1 mM EDTA, 1% NP40, 1 mM PMSF, 5 µg/ml aprotinin, 5 µg/ml leupeptin). The sample were lysed on ice with occasional vortex for 30 min, and then centrifuged at 14,000 rpm for 15 min at 4° C. The supernatant were collected and denatured at 95° C. in sample buffer for 5 min. The denatured samples were then separated on 15% SDS-PAGE gels and transferred to PVDF membrane. Membranes were then blocked with 5% non-fat milk and probed with appropriate primary and secondary antibodies. The protein signals were finally visualized with ECL kit and the protein bands density were quantified by ImageJ program.

Primary neuron culture

The E16 pregnant rat was anesthetized by intraperitoneal injection with 3% chloral hydrate in normal saline (1 ml/100 g bdw). The uterus containing embryos were dissected and transferred to a Petri dish, and then the embryos were collected on a new petri dish containing ice cold PBS. The brains of the embryos were then dissected under stereoscope and the cortices of the brains were placed in a Petri dish containing ice cold 10% FBS DMEM. The meninges of the cortices were removed carefully and then transferred to a 15 ml tube. Total 5 ml of digestion solution (1.25% Trypsin diluted with DMEM/F12 medium) were added into the tube containing meninges-free cortices and then incubated at 37° C. for 15 min. The digestion was stopped by adding 10% FBS DMEM/F12 supplemented with 10 µg/ml DNase (Sigma, DN25). The solution of tissue mixture were then pipetted up and down thoroughly to dissociate the cells until no obvious tissue blocks were observed and the tissue mixture can pass the tip of the pipet easily. After dissociation, the tissue mixture was passed through a 70 µm filter (BD Falcon, USA) into a 50 ml tube. The filtrate was centrifuged at 800 rpm at room temperature for 3 min, the supernatant was decanted and then the cells were re-suspended with Neurobasal medium (Invitrogen, 21103049) supplemented with B27 supplement (Gibco, 17504), 25 µM L-Glutamic acid (sigma, G1251) and 1% PSN (15640-055). For cell counting, total 10 µl of the re-suspended cells were diluted 10 times with typan blue. The viable cells without staining with typan blue were then counted under microscope. The cells were seeded on poly-D-lysine (Sigma, P0988) pretreated culture plates. For imaging, the cells were seeded in a low density ($1\times10^5$ cells/well of 24-well plate). For biochemistry analysis, the cells were seeded in a high density ($3\times10^6$ cells/well of 6-well plate). Twelve hours later, medium were replaced completely by Neurobasal medium supplemented with B27, 2 mM L-Glutamine (Gibco, 25030) and 1% PSN. Three days later, 5 µM Ara-C(Sigma, C6645) was added. The medium was half changed 24 hrs later. Cultures were fed every 3 days by half-replacement of the old medium with fresh medium. Cultures were maintained for at least seven days for neuron differentiation and maturation.

Preparation of drug-containing fly food

TGY and/or rotenone was dissolved in water and mixed thoroughly with rehydrated instant Drosophila medium (Carolina, USA). The medium was renewed every 3 days.

Drosophila culture and strains

Fly stocks were raised at 25° C. on standard cornmeal medium, under 50%-70% relative humidity with 12 hrs dark-light cycle. The following Drosophila strains were obtained from Bloomington Drosophila Stock Center and used in the study: w$^{1118}$ as wild type; elav-GAL4, which drive transgene expression in all neurons; Ddc-GAL4 that drive transgene expression in dopaminergic neurons; UAS-SNCA$^{wt}$ that carrying the wild type human SNCA gene; Cg-GAL4 that drives transgene expression in Drosophila fat body and UAS-Atg8a-GFP.

Immunoblotting analysis of Drosophila samples

Twenty fly heads were homogenized in lysis buffer (50 mM Tris, 1% NP-40, 0.35% sodium deoxycholate, 150 mM NaCl, 1 mM EDTA, 1 mM EGTA, 1 mM PMSF, pH7.4) and lysed on ice for 20 min. The supernatants were collected after centrifugation (14,000 rpm, 10 min, 4° C.) and denatured with 5× Laemmli sample buffer and then separated on 12% SDS-PAGE gels. The protein on the gels were then transferred to PVDF membranes (GE Healthcare, RPN303F) and processed for immunoblotting. Membranes were blocked with 5% nonfat milk and probed with primary and secondary antibodies. The bands were developed with an ECL kit (Pierce, 32106). The density of the bands was quantified by densitometry (ImageJ, NIH).

Confocal analysis of Atg8a-EGFP puncta in Drosophila fat body

Crossed flies were allowed to lay eggs for 1 hr, 90 hrs later, the L3 larvae were collected for further treatment. The compounds were firstly dissolved in DMSO and then diluted to the desired concentration with ddH$_2$O and then mixed thoroughly with instant fly food. The L3 larvae were placed in the prepared food and received treatment for 6 hrs. After treatment, the fat body lobes of the larvae were harvested with fine forceps and fixed with 4% PFA in PBS at room temperature for 15 min. Fat body lobes were then washed with PBS three times and subsequently mounted with VECTASHIELD hardset antifade mounting medium. The slides were then subjected to confocal microscopy analysis.

Statistics analysis

Each experiment was repeated at least three times. The data was expressed as means±SD. Student-t test or One-way ANOVA followed by Dunnett's multiple comparison tests were conducted. All statistics analyses were performed in GraphPad Prism6 (GraphPad Software, Inc.).

INDUSTRIAL APPLICABILITY

The present invention discloses novel synthetic compositions including Cory B analogues and tetracyclic oxindole alkaloids that induce autophagy in neurons to degrade protein aggregates both in vivo and in vitro and the application thereof in treating diseases that can benefit from autophagy inducement.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

What we claim:

1. A composition comprising a therapeutically effective amount of a compound of formula CB6, a pharmaceutically acceptable salt thereof or a combination thereof:

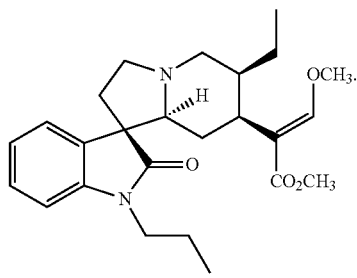
(CB6)

2. The composition according to claim 1, wherein said composition further comprises one or more other therapeutic agent.

3. The composition of claim 1, wherein said composition further comprises one or more of a pharmaceutically acceptable carrier, solvent, excipient, adjuvant, and other therapeutic agent.

4. The composition according to claim 1, wherein said composition is in a form comprising solution, solid, tablet, capsule, powder, paste and aerosol.

5. The composition of claim 2, wherein said one or more other therapeutic agent comprises rapamycin.

6. A composition comprising a therapeutically effective amount of a compound of formula III, a pharmaceutically acceptable salt thereof or a combination thereof:

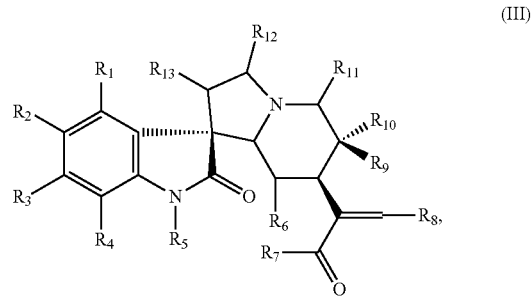
(III)

wherein $R_1$, $R_2$, $R_3$, $R_4$, $R_6$, $R_{10}$, $R_{11}$, $R_{12}$ and $R_{13}$ are hydrogen; $R_7$ and $R_8$ are methoxy group; $R_9$ is ethyl group and $R_5$ is selected from propyl group and allyl group.

7. The composition of claim 6, wherein said composition comprising a therapeutically effective amount of a compound of

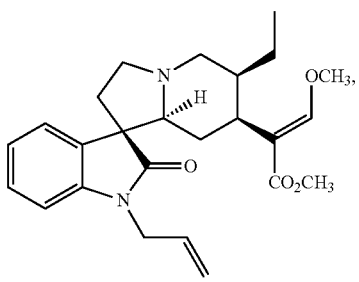
(CB8)

a pharmaceutically acceptable salt thereof or a combination thereof.

8. The composition according to claim 7, wherein said composition further comprises rapamycin.

9. The composition of claim 6, wherein said composition comprising a therapeutically effective amount of a compound of

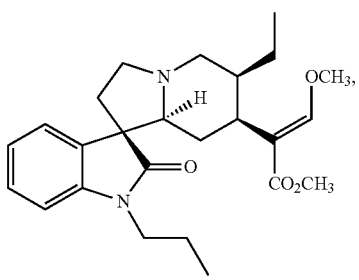
(CB6)

a pharmaceutically acceptable salt thereof or a combination thereof.

* * * * *